US011116242B2

(12) United States Patent
Møller et al.

(10) Patent No.: US 11,116,242 B2
(45) Date of Patent: Sep. 14, 2021

(54) BEVERAGES CONTAINING BARLEY β-GLUCAN

(71) Applicants: Carlsberg Breweries A/S, Copenhagen V (DK); University of Copenhagen, Copenhagen K (DK)

(72) Inventors: Birthe Møller, Kerteminde (DK); Mette Skau Mikkelsen, Hillerød (DK); Morten Georg Jensen, Roskilde (DK); Zoran Gojkovic, Holte (DK)

(73) Assignees: Carlsberg Breweries A/S, Copenhagen V (DK); University of Copenhagen, Copenhagen K (DK)

( * ) Notice: Subject to any disclaimer, the term of this patent is extended or adjusted under 35 U.S.C. 154(b) by 131 days.

(21) Appl. No.: 16/097,345

(22) PCT Filed: May 2, 2017

(86) PCT No.: PCT/EP2017/060376
§ 371 (c)(1),
(2) Date: Oct. 29, 2018

(87) PCT Pub. No.: WO2017/191109
PCT Pub. Date: Nov. 9, 2017

(65) Prior Publication Data
US 2019/0133152 A1     May 9, 2019

(30) Foreign Application Priority Data
May 2, 2016   (DK) .................................. 2016 70285

(51) Int. Cl.
| | |
|---|---|
| C12C 7/04 | (2006.01) |
| C12C 5/00 | (2006.01) |
| C12C 7/047 | (2006.01) |
| A23L 2/38 | (2021.01) |
| A23L 2/52 | (2006.01) |
| A23L 2/66 | (2006.01) |
| C12C 12/02 | (2006.01) |
| A61P 9/10 | (2006.01) |
| A61K 31/716 | (2006.01) |
| C12C 12/00 | (2006.01) |

(52) U.S. Cl.
CPC .................. *A23L 2/382* (2013.01); *A23L 2/38* (2013.01); *A23L 2/52* (2013.01); *A23L 2/66* (2013.01); *A61K 31/716* (2013.01); *A61P 9/10* (2018.01); *C12C 5/004* (2013.01); *C12C 5/006* (2013.01); *C12C 7/04* (2013.01); *C12C 7/047* (2013.01); *C12C 12/00* (2013.01); *C12C 12/02* (2013.01); *A23V 2002/00* (2013.01); *A23V 2200/32* (2013.01); *A23V 2200/326* (2013.01); *A23V 2200/328* (2013.01)

(58) Field of Classification Search
None
See application file for complete search history.

(56) References Cited

U.S. PATENT DOCUMENTS

| | | | |
|---|---|---|---|
| 2002/0081367 A1 | 6/2002 | Triantafyllou | |
| 2004/0170726 A1* | 9/2004 | Triantafyllou | .......... C12C 12/00 426/100 |
| 2004/0258829 A1* | 12/2004 | Zheng | .................... A23L 7/126 426/615 |
| 2006/0064780 A1 | 3/2006 | Munck et al. | |
| 2009/0117630 A1 | 5/2009 | Olsen et al. | |
| 2012/0034341 A1 | 2/2012 | Chen et al. | |
| 2015/0216217 A1 | 8/2015 | Devaux et al. | |

FOREIGN PATENT DOCUMENTS

| | | |
|---|---|---|
| CA | 2717784 A1 | 9/2009 |
| CN | 103834709 A | 6/2014 |
| EP | 0251798 A1 | 1/1988 |
| JP | 2006521828 A | 9/2006 |
| JP | 2015 186477 A1 | 10/2015 |
| WO | WO 00/24270 | 5/2000 |
| WO | WO 00/24864 | 5/2000 |
| WO | WO 02/37955 A1 | 5/2002 |
| WO | 2004086878 A2 | 10/2004 |
| WO | WO 2005/059084 A1 | 6/2005 |
| WO | WO 2006/105651 A | 10/2006 |
| WO | WO 2009/028225 A1 | 3/2009 |
| WO | WO 2012/103594 A1 | 8/2012 |

(Continued)

OTHER PUBLICATIONS

English machine translation of CN 103834709, downloaded form translationportal.epo.org (Year: 2014).*
Steiner et al., "Comparison of beer quality attributes between beers brewed with 100% barley malt and 100% barley raw material" J Sci Food Agric vol. 92 pp. 803-813 (Year: 2011).*
Mikkelsen et al., "Barley genotypic beta-glucan variation combined with enzymatic modifications direct its potential as a natural ingredient in a high fiber extract" Journal of Cereal Science vol. 75 pp. 45-53 (Year: 2017).*
Bae et al., Effect of enzymatic hydrolysis on cholesterol-lowering activity of oat b-glucan, New Biotechnology, vol. 27, No. 1, 2010.
Christensen & Scheller, Regulation of (1,3;1,4)-b-D-glucan synthesis in developing endosperm of barley iys mutants, Journal of Cereal Science 55 (2012) 69-76.

(Continued)

*Primary Examiner* — Eric Olson
(74) *Attorney, Agent, or Firm* — McNeill Baur PLLC

(57) ABSTRACT

The invention relates to methods for preparing a beverage comprising at least 2 g/L β-glucan, wherein said β-glucans have an average molecular weight in the range of 80 to 200 kDa. The methods involve mashing barley kernels comprising at least 10% β-glucans and having a ratio of DP3/DP4 in said β-glucan of at least 3 in the presence of α-amylase and endo-1,3(4)-β-glucanase activity. The beverages have a viscosity providing a good mouth-feel, and at the same time they comprise β-glucans, which are able to aid in lowering LDL cholesterol levels. The beverages are generally stable and can be stored for months at room temperature without a significant decrease in β-glucan content.

20 Claims, 8 Drawing Sheets
Specification includes a Sequence Listing.

(56) References Cited

FOREIGN PATENT DOCUMENTS

| WO | WO 2015/017901 A1 | 2/2015 |
|---|---|---|
| WO | WO 2015/032850 A1 | 3/2015 |

OTHER PUBLICATIONS

Cui et al., Physicochemical properties and structural characterization by two-dimensional NMR spectroscopy of wheat b-D-glucan—comparison with other cereal b-D-glucans, Carbohydrate Polymers 41 (2000) 249-258.

Howard et al., Use of advanced recombinant lines to study the impact and potential of mutations affecting starch synthesis in barley, Journal of Cereal Science 59 (2014) 196e202.

Jacobsen et al., A chemometric evaluation of the underlying physical and chemical patterns that support near infrared spectroscopy of barley seeds as a tool for explorative classification of endosperm genes and gene combinations, Journal of Cereal Science 42 (2005) 281-299.

Keenan et al., The effects of concentrated barley b-glucan on blood lipids in a population of hypercholesterolaemic men and women, British Journal of Nutrition (2007), 97, 1162-1168.

Lazaridou et al., A comparative study on structure—function relations of mixed-linkage (1 -> 3), (1 -> 4) linear b-D-glucans, Food Hydrocolloids 18 (2004) 837-855.

Mikkelsen et al., Molecular structure of large-scale extracted b-glucan from barley and oat: Identification of a significantly changed block structure in a high b-glucan barley mutant, Food Chemistry 136 (2013) 130-138.

Munck & Jespersen, From Discovery of High Lysine Barley Endosperm Mutants in the 1960-70s to new Holistic Spectral Models of the Phenome and of Pleiotropy in 2008, Q.Y. Shu (ed.), Induced Plant Mutations in the Genomics Era. Food and Agriculture Organization of the United Nations, Rome, 2009, 419-422.

Munck & Jespersen, The Multiple Uses of Barley Endosperm Mutants in Plant Breeding for Quality and for Revealing Functionality in Nutrition and Food Technology, Q.Y. Shu (ed.), Induced Plant Mutations in the Genomics Era. Food and Agriculture Organization of the United Nations, Rome, 2009, 182-186.

Patron et al., The lys5 Mutations of Barley Reveal the Nature and Importance of Plastidial ADP-Glc Transporters for Starch Synthesis in Cereal Endosperm, Plant Physiology, 2004, vol. 135, pp. 2088-2097.

Rudi et al., Genetic variability in cereal carbohydrate compositions and potentials for improving nutritional value, Animal Feed Science and Technology 130 (2006) 55-65.

Seefeldt et al., Accumulation of mixed linkage (1/3) (1/4)-b-D-glucan during grain filling in barley: A vibrational spectroscopy study, Journal of Cereal Science 49 (2009) 24-31.

* cited by examiner

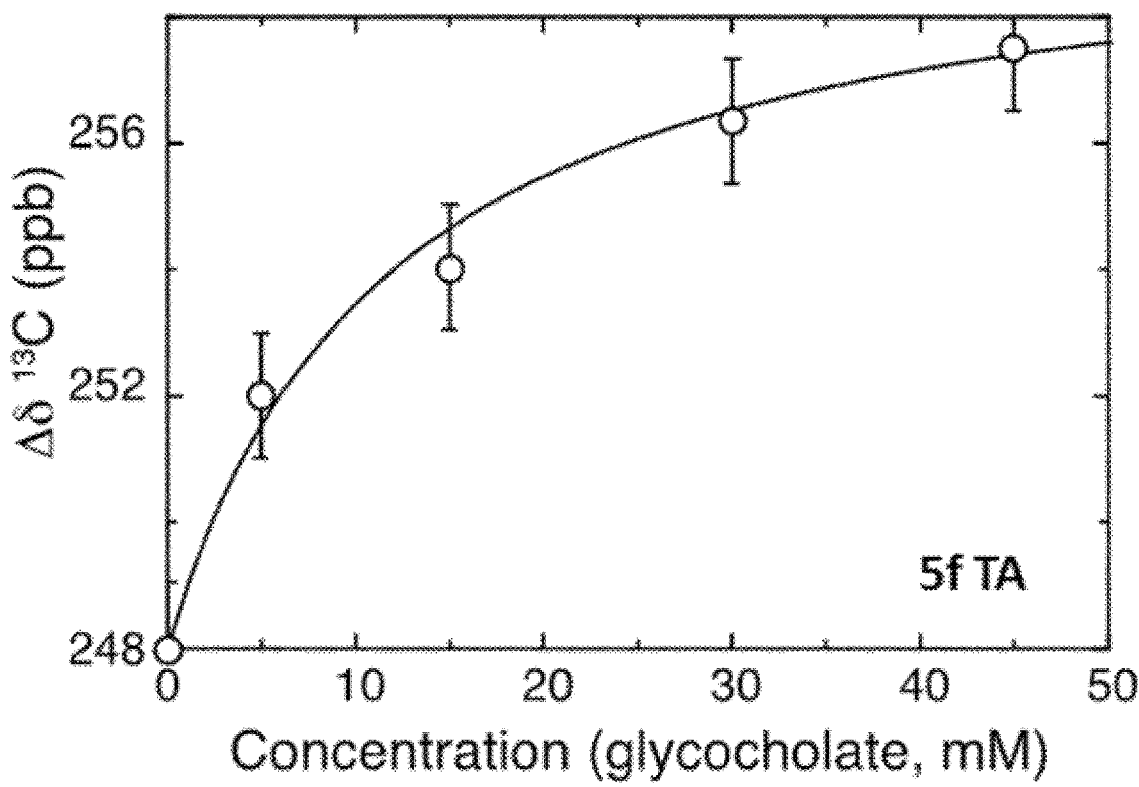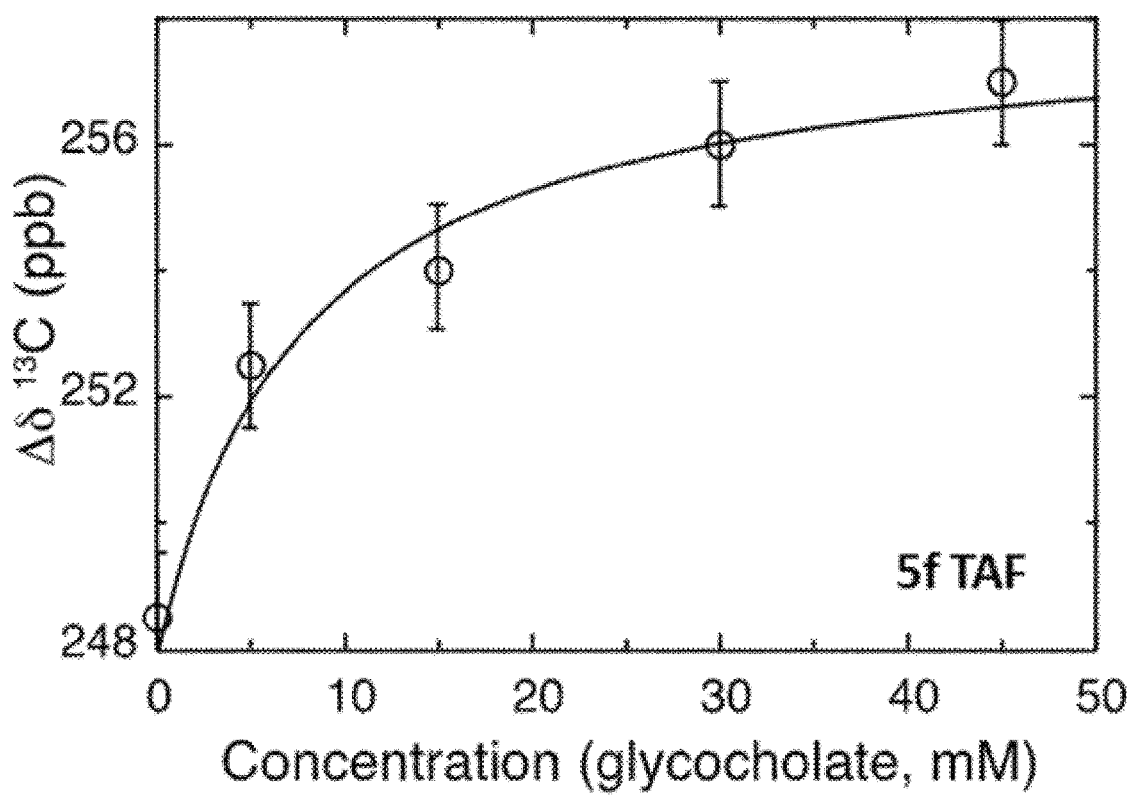
Fig. 3

```
1                                                              50
(1)   MAAAMAATTMVTKNNGGSLAMDKKNWFFRPALEVAESMSSQP-ESRSLEF
(1)   MAATMAVTTMVTRS---------KESWSSLQVPAVAEPWKPRGGKTGGLEF
      51                                                     100
(50)  PRRALFASVGLSLSHDG---------------KARPADDVAHQLAAAGDAG
(43)  PRRAMFASVGLNVCPGVPAGRDPREPDPKVVRAADNCDIAASLAPPFPGS
      101                                                    150
(86)  VQQTQKAKKAKKQQLGLRKVRVKIGN---------------PHLRRLVSGA
(93)  RPPGRRGRGSEEEEAEGRRHEEAAAAGRSEPEEGQGDRQPAPARLVSGA
                                                             200
(122) IAGAVSRTFVAPLETIRTHLMVGSSGADSMGGVFRWIMRTEGWPGLFRGN
(143) IAGAVSRTFVAPLETIRTHLMVGSIGVDSMAGVFQWIMQNEGWTGLFRGN
      201                                                    250
(172) AVNVLRVAPSKAIEHFTYDTAKKYLTPEAGEPAKVPIPTPLVAGALAGVA
(193) AVNVLRVAPSKAIEHFTYDTAKKDLTPKGDEPPKIPIPTPLVAGALAGFA
      251                                                    300
(222) STLCTYPMELVKTRLTIEKDVYDNLHAFVKIVRDEGPGELYRGLAPSLI
(243) STLCTYPMELIKTRVTIEKDVYDNVAHAFVKILRDEGPSELYRGLTPSLI
      301                                                    350
(272) GVVPYAAANFYAYETLRGAYRRASGKE---DVGNVPTLLIGSAAGAIAST
(293) GVVPYAACNFYAYETLKRLYRRATGRRPGADVGPVATLLIGSAAGAIASS
      351                                                    400
(319) ATFPLEVARKQMQVGAVGGRQVYKNVLHAMYCIINKEGAAGLYRGLGPSC
(343) ATFPLEVARKQMQVGAVGGRQVYQNVLHAIYCILKKEGAGGLYRGLGPSC
      401                                   444
(369) IKLMPAAGISFMCYEACKKILIENNQEA
(393) IKLMPAAGIAFMCYEACKKILVDKEDEEEEDEAGGGEDDKKKVE
```

Fig. 10

BEVERAGES CONTAINING BARLEY β-GLUCAN

CROSS-REFERENCE TO RELATED APPLICATIONS

This application is a national phase entry pursuant to 35 U.S.C. § 371 of International Application No. PCT/EP2017/060376, filed Mar. 1, 2017, which claims the benefit of priority of Denmark Application No. PA 2016 70285, filed May 2, 2016, each of which is incorporated by reference herein in its entirety for any purpose.

SEQUENCE LISTING

The present application is filed with a Sequence Listing in electronic format. The Sequence Listing is provided as a file entitled "2018-10-25_01130-0010-00US_Seq_List.txt" created on Oct. 25, 2018, which is 19,793 bytes in size. The information in the electronic format of the sequence listing is incorporated herein by reference in its entirety.

FIELD OF INVENTION

The present invention relates to the field of health drinks as well as to methods for producing same. In particular the invention relates to methods for producing beverages and beverage bases having a high level of barley β-glucans.

BACKGROUND OF INVENTION

β-Glucans have a remarkable range of health benefits, including the promotion of heart health, healthy blood glucose levels and weight loss. β-Glucans are the soluble fibers found in cereal grains and are large linear polysaccharides of glucose units, connected by (1→3) or (1→4)-β-linkages. Of all cereal grains, barley is the richest source of β-glucan fiber.

However, liquids containing high levels of β-glucans are generally very viscous and thus less suitable as beverages.

SUMMARY OF INVENTION

Thus, there is an unmet need for methods and materials for preparing beverages having a natural high β-glucan content.

The present invention discloses that by employing barley grains having a high ratio of DP3 to DP4, and treating extracts of such barley grains with an enzyme mixture comprising α-amylase, and endo-1,3(4)-β-glucanase activity, and optionally glucoamylase and/or pullulanase activity, then it is possible to prepare stable beverages having a viscosity providing a good mouth-feel, and at the same time comprising β-glucans, which are able to aid in lowering LDL cholesterol levels. The beverages are preferably stable and can be stored for months at room temperature without a significant decrease in β-glucan content.

Thus, the invention provides methods for preparing a beverage comprising at least 2 g/L β-glucan, wherein said β-glucans have an average molecular weight in the range of 80 to 200 kDa, said method comprising the steps of
  a) providing kernels of a barley plant, wherein said kernels have the following characteristics:
    i. comprising at least 10% β-glucans
    ii. having a ratio of DP3/DP4 in said β-glucan of at least 3
  b) mashing said kernels with water in the presence of an enzyme composition, wherein said composition comprise α-amylase, and endo-1,3(4)-β-glucanase activity, thereby obtaining an aqueous extract
  c) separating said aqueous extract from the barley kernels, thereby obtaining a beverage or a beverage base
  d) optionally processing the beverage base into a beverage.

The invention also provides beverages comprising at least 2 g/L β-glucans, wherein said β-glucans have an average molecular weight in the range of 80 to 200 kDa and wherein said beverage is produced by the methods of the invention.

The invention further provides beverages according to the invention for reducing the risk of acquiring a clinical condition in an individual in need thereof, wherein the clinical condition is selected from the group consisting of coronary heart disease, and diabetes.

The invention also provides methods for reducing the risk of acquiring a clinical condition in an individual in need thereof, wherein the clinical condition is selected from the group consisting of coronary heart disease, diabetes and infections, said method comprising administering the beverages of invention to said individual in an effective amount.

The invention also provides methods for reducing blood levels of at least one lipid selected from the group consisting of triglycerides, cholesterol, and LDL in an individual in need thereof, wherein said method comprises intake of the beverage according to to the invention by said individual.

The invention also provides methods for reducing the risk of obesity or reducing obesity in an individual in need thereof, said method comprising intake by said individual of the beverage according to the invention.

DESCRIPTION OF DRAWINGS

FIG. 3: Langmuir adsorption curves for β-glucans; lys5f TA (530 kDa) and lys5f TAF (150 kDa) upon addition of increasing glycocholate concentrations (0, 5, 15, 30, 45 mM) at pH 5.

FIG. 10: alignment between HvNST1 and maize BT1.

DETAILED DESCRIPTION OF THE INVENTION

Definitions

Figure 1:
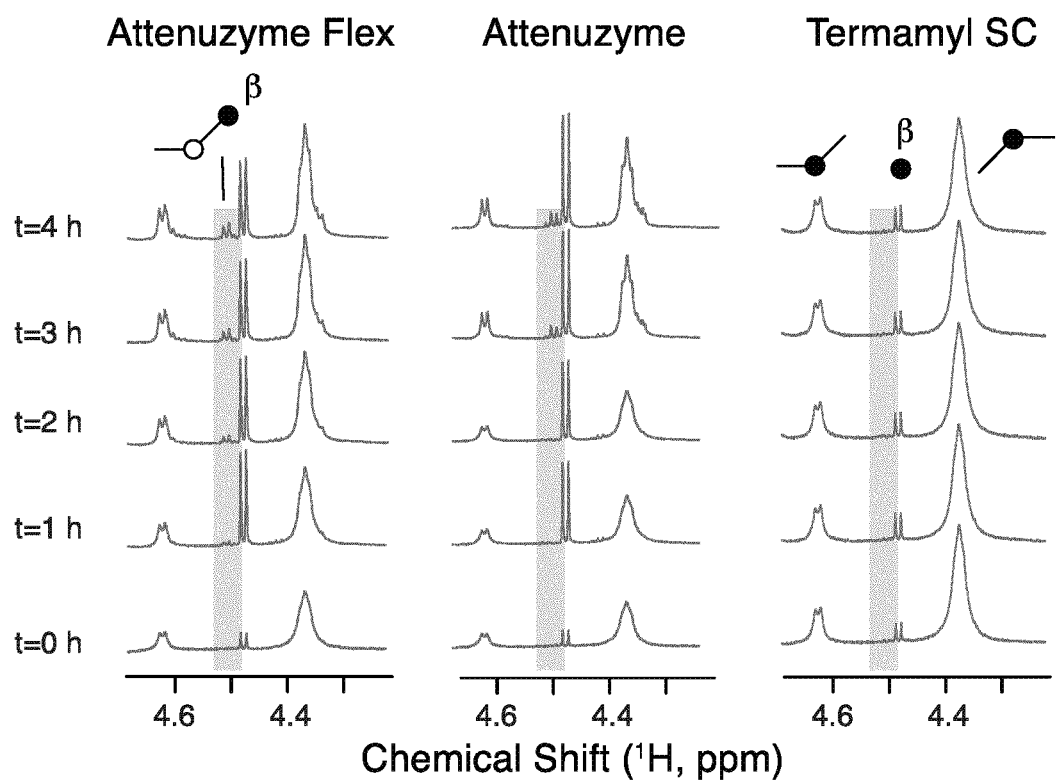
FIG. 1: End products of β-glucan degradation (medium viscosity barley β-glucan from Megazyme) by Attenuzyme® Flex, Attenuzyme® and Termamyl® SC at 18° C.

As used herein, "a" can mean one or more, depending on the context in which it is used.

As used herein in relation to amount, then the term "approximately" means+/−5%, preferably +/−2%, even more preferably +/−1%.

The term "beer" as used herein refers to a beverage prepared by fermentation of wort. Preferably, said fermentation is done by yeast.

The term "mixed linkage β-glucan" as used herein refers to polysaccharides of D-glucose monomers linked by β-(1→3) or (1→4) glycosidic bonds. Both types of glycosidic bonds may occur within one polysaccharide. The terms β-glucan and beta-glucan are used interchangeably herein. The term "β-glucan" as used herein may refer to any β-glucan, but preferably the term "β-glucan" refers to "mixed linkage β-glucan".

The term "beverage base" as used herein refers to a liquid, which can be processed into a finished ready-to-drink beverage. In general a beverage base can be processed into a finished beverage by addition of one or more additional compounds and/or additional liquids and/or by fermentation.

The term "kernel" is defined to comprise the cereal caryopsis, also denoted internal seed, the lemma and palea. In most barley varieties, the lemma and palea adhere to the caryopsis and are a part of the kernel following threshing. However, naked barley varieties also occur. In these, the caryopsis is free of the lemma and palea and threshes out free as in wheat. The terms "kernel" and "grain" are used interchangeably herein.

"Mashing" is the incubation of barley kernels or malt in water at defined temperature(s). Frequently the barley kernels have been milled prior to incubation with water.

A "ratio of water to barley kernels/milled barley" of 1 to X, mean 1 part water to X parts barley kernels or milled barley. Ratios may also be indicated as 1 to in the range of XX to YY, meaning 1 part water and in the range of XX to YY parts barley kernels or milled barley. All ratios are given as weight per weight ratios.

By the term "wort" is meant a liquid extract of barley kernels prepared by mashing. Other adjuncts may be mixed with the barley kernels and mashed in order to arrive at the wort. Adjuncts may also be added to wort. Adjuncts may be any starch-containing material, such as other cereals than barley, malt or syrups.

A Method for Preparing a Beverage

The present invention relates to a method for preparing a beverage having a natural high β-glucan content. Said beverage may be any of the beverages described herein below in the section "Beverage".

The method involves mashing grains of a barley plant in water in the presence of an enzyme composition comprising α-amylase and endo-1,3(4)-β-glucanase activity, and optionally also glucoamylase and/or pullulanase activity. In one embodiment of the invention said kernels of a barley plant have preferably not been subjected to any heat treatment prior to mashing. In particular, it may be preferred that the kernels have not been malted. It is generally preferred that said kernels of a barley plant have been milled prior to mashing. Said kernels have a high level of β-glucans (preferably at least 10%) and a high ratio of DP3/DP4 in said β-glucan (preferably at least 3). The barley plant may be any of the barley plants described herein below in the section "Barley plant". Mashing involves incubating barley kernels, preferably milled barley kernels with water at defined temperature(s). Mashing may be performed in any of the ways described herein below in the section "Mashing". The enzyme composition comprises α-amylase and endo-1,3(4)-β-glucanase activity and optionally also glucoamylase and/or pullulanase activity. Said activities may be derived from one or more enzymes. Thus, it is not required that the enzyme composition comprises 3 or 4 different enzymes, if some of the enzymes have more than one activity. In general however, the enzyme composition comprises an enzyme with α-amylase activity, an enzyme with pullulanase activity and an enzyme with endo-1,3(4)-β-glucanase activity and an enzyme with glucoamylase activity. Said enzyme composition may be any of the enzyme compositions described herein below in the section "Enzyme composition".

After mashing, the aqueous extract is separated from the barley kernels. Said aqueous extract may also be referred to as "wort" herein. The aqueous extract may be ready to consume as a beverage according to the invention. However, frequently the aqueous extract needs to be further processed into a beverage. In such cases the aqueous extract may also be referred to as "beverage base" herein. The beverage base may be processed into a beverage by any of the methods described herein below in the section "Processing beverage base into a beverage".

Thus, one object of the invention is to provide methods for preparing any of the beverages described herein below in the section "Beverage", said method comprising the steps of
  a) providing kernels of a barley plant, which may be any of the barley plants described herein below in the section "Barley plant";
  b) mashing said kernels in any of the ways described herein below in the section "Mashing" in the presence of an enzyme composition, which may be any of the composition described herein below in the section "Enzyme composition", thereby obtaining an aqueous extract
  c) separating said aqueous extract from the barley kernels, thereby obtaining a beverage or a beverage base
  d) optionally processing the beverage base into a beverage in any of the ways described herein below in the section "Processing beverage base to a beverage".

Beverage

The invention relates to methods for preparing a beverage having a high content of β-glucan, but in the same time having a viscosity, which is sufficiently low to render a good mouth feel to the beverage.

Barley β-glucans have been shown to lower/reduce blood cholesterol. According to the European Food Safety Organisation EFSA, then the beneficial effect may be obtained with a daily intake of 3 g of barley β-glucan. The beneficial effect may also be obtained by intake of a food product containing at least 1 g of β-glucans per quantified portion. Accordingly, it is preferred that the beverages of the invention contain sufficient β-glucan in order to allow a daily intake of at least 3 g. Thus in one embodiment the beverages of the invention contains in the range of 0.5 to 2 g, such as in the range of 0.5 to 1.5 g, for example approximately 1 g, such as 1 g β-glucans per serving. In the context of the beverages of the present invention, then a serving is typically either 250 or 330 ml. Thus, the beverages of the invention preferably contain afore-mentioned levels of β-glucans per 250 to 330 ml, for example per 250 ml and/or per 330 ml.

Thus, the beverages prepared by the present invention preferably comprise at least 2 g/L β-glucans. More preferably the beverages contain at 3 g/L β-glucans. Yet more preferably the beverages contain at least 4 g/L β-glucans. It is also comprised within the invention that the beverages may comprise more β-glucans, such as in the range of 4 to 20 g/L, such as in the range pf 4 to 15 g/L for example in the range of 4 to 10 g/L. The beverage may also be a beverage concentrate containing a very high amount of β-glucans, such as more than 8 g/L, for example 8 to 20 g/L. Such concentrates may potentially be diluted prior to intake.

The level of β-glucan in the final beverage may be adjusted in several ways. One method for adjusting the level of β-glucan in the beverage is by adjusting the ratio of barley kernels to water during mashing. Useful ratios of barley kernels to water, which can be used with the methods of the invention are disclosed in the section "Mashing" herein below. In order to arrive at a lower content of β-glucan the beverage base may also be diluted with an additional liquid.

The invention discloses that β-glucans with a low molecular weight have beneficial health effects, i.e. that β-glucans with low molecular weight are capable of reducing blood cholesterol and in particular are capable of reducing blood LDL levels.

Furthermore, the invention shows that beverages containing low molecular weight β-glucans also have a low viscosity.

Accordingly, it is preferred that the beverages prepared by the methods of the invention comprise β-glucans having an average low molecular weight in the range of 80 to 200 kDa. For example said β-glucans may have an average molecular weight in the range of 110 to 190, such as in the range of 120 to 180, for example in the range of 130 to 170, such as in the range of 140 to 160. In one embodiment the beverages prepared by the methods of the invention comprise β-glucans having an average molecular weight of approximately 150.

The average molecular weight is preferably determined in comparison to β-glucan standards. Such β-glucan standards are commercially available e.g. they may be acquired from Megazyme, Ireland. The molecular weight may be determined by any useful method, e.g. by conventional size exclusion chromatography using β-glucan standards, for example using asahipak from Shodex, US. A preferred method for determining molecular weight is outlined herein below in Example 5a.

The low molecular weight β-glucans comprised in the beverages of the present invention have beneficial health effects to the same extend as a medium size β-glucan (530 kDa) extracted under similar conditions. For example said β-glucans are preferably capable of binding bile salts, such as glycocholate. Preferably, said β-glucans are capable of binding bile salts, such as glycocholate through direct molecular interactions. Binding to bile salts may for example be determined by determining signal changes ($\Delta\delta$) between two β-glucan resonances, wherein changes indicate direct interactions between β-glucans and the bile salt in solution as described herein below in Example 6. Thus, the β-glucans comprised in the beverages may have an increase in $\Delta\delta^{13}C$ of at least 5 ppb, such as at least 7 ppb upon addition of 50 mM glycocholate when determined as described in Example 6.

As mentioned above it is also preferred that the beverage has a sufficiently low viscosity in order to render a good mouth feel to the beverage. Thus, it is preferred that the beverage has a viscosity of at the most 55 mPas, for example at the most 50 mPas, such as of the most 40 mPas, for example at the most 35 mPas. The viscosity may be determined using any standard viscometer. In particular, the viscosity may be determined as described in Example 5a.

The beverages according to the present invention are preferably stable, i.e. the β-glucan content does not decrease significantly upon storage. Thus, it is preferred that the β-glucan content of the beverages of the invention does not decrease by more than 5%, for example do not decrease by more than 3% upon storage at room temperature for 6 months. Said beverages may comprise a stabiliser to prevent β-glucan precipitation, e.g. in the range of 0.01 to 0.050% stabiliser, e.g. 0.025% gellan gum as described below.

The beverage of the invention may be the aqueous extract obtained after mashing barley kernels in the presence of the enzyme composition. This aqueous extract may also be referred to as wort herein. However, the beverage may also be a beer like beverage, prepared by fermenting the aqueous extract with a microorganism, e.g. with yeast. The beverage may also be a mixture of the aqueous extract with one or more additional liquids. The beverage may also be the aqueous extract to which one or more additional compounds have been added.

Mashing

The methods of the invention comprise a step of mashing barley kernels in the presence of an enzyme composition.

Mashing is the incubation of barley kernels with water at defined temperature(s). Mashing can thus be considered as a method for preparing an aqueous extract of barley kernels. In order to make the aqueous extraction as efficient as possible, it is preferred that the barley kernels are broken up prior to mashing. It is preferred that the barley kernels are milled prior to mashing to prepare a barley flour, and that the mashing is done using said barley flour. Milled barley kernels may be referred to as "milled barley", "milled barley kernels" or "barley flour" herein.

The barley kernels e.g. the milled barley kernels are then incubated with water. Thus, step b) of the method may comprise mixing milled barley kernels with water. The ratio of barley kernels to water may be selected in order to arrive at a desirable concentration of β-glucans in the aqueous extract. In general, the higher the ratio of barley kernels to water, the higher the level of β-glucan in the beverage.

Since it is preferred that the level of β-glucans in the beverage is at least 2 g/L, then it is preferred that the ratio of barley kernels to water is sufficiently high to obtain such a level of β-glucans.

Accordingly, it is preferred that the ratio of water to barley kernels is 1 to at least 10, for example 1 to at least 12, such as 1 to at least 15. In particular, the ratio of water to barley kernels may be 1 to in the range of 10 to 20, such as 1 to in the range of 12 to 18. In one embodiment of the invention the ratio of water to barley kernels is 1 to approximately 15. Said ratio is preferably the w/w ratio of water to the dry weight of said barley kernels.

In embodiments of the invention where mashing involves incubating milled barley with water, then it is preferred that the ratio of water to milled barley is 1 to at least 10, for example 1 to at least 12, such as 1 to at least 15. In particular, the ratio of water to milled barley may be 1 to in the range of 10 to 20, such as 1 to in the range of 12 to 18. In one embodiment of the invention the ratio of water to milled barley is 1 to approximately 15.

Incubation of barley kernels (e.g. milled barley) with water is preferably performed at a specific temperature. The temperature may be of importance, as it may affect enzyme activity.

Mashing can occur in the presence of adjuncts, which is understood to comprise any carbohydrate source other than barley kernels, such as, but not limited to, barley, barley syrups, maize, rice, sorghum, rye, oats or wheat—either as whole kernels or processed products like grits, syrups or starch. All of the aforementioned adjuncts may be used principally as an additional source of extract (syrups are typically dosed after mashing).

The mashing water may comprise one or more additional compounds, e.g. salts or pH regulating agents. Non-limiting examples of pH regulating agents include buffers and acids, e.g. phosphate buffer or phosphoric acid. A non-limiting example of useful salts include calcium chloride.

Typically, the mashing comprises or even consists of incubation at a temperature in the range of 60 to 72° C., such as a temperature in the range of 60 to 70° C., for example a temperature in the range of 62 to 68° C., for example a temperature in the range of 64 to 66° C., such as a temperature of approximately 65° C. The barley kernels, for example milled barley may be mixed with water at any specific stage, but may frequently be added to the water, once the water has reached aforementioned temperature.

Incubation at said temperature may be for any desirable length of time, typically for in the range of 30 to 120 min, preferably in the range of 30 to 60 min., such as for approximately 45 min.

Before or during incubation the pH may be adjusted. E.g. the pH may be adjusted to in the range of 5 to 7, such as in the range of 5 to 6, for example to approximately 5.48.

In the methods according to the invention mashing is performed in the presence of an enzyme composition comprising α-amylase and endo-1,3(4)-β-glucanase activity, and optionally also a glucoamylase and/or pullulanase, which may be any of the enzyme compositions described herein below in the section "Enzyme composition". Said enzyme composition may be added before or during mashing. Typically, it is added once the mash or the water for mashing has been adjusting to the above-mentioned temperature levels. The beverages prepared according to the present invention contain β-glucans of a specific molecular weight. Mashing with the enzyme composition according to the invention may influence the molecular weight. Accordingly it is preferred that the mashing in the presence of the enzyme composition is performed for a length of time and at a temperature, which results in β-glucans having an average molecular weight in the range of 80 to 200 kDa. This may be ensured by taking samples of the aqueous extract at specific times during mashing and under different temperature conditions, followed by measuring the average molecular weight of the β-glucan therein. In that way, the skilled person will be able to select an adequate time and temperature for mashing. In one embodiment the time and temperature is selected as described above.

At the end of the mashing procedure it is frequently desirable to heat the water/barley kernel/enzyme composition mixture to at least 75° C. This may have several effects including inactivation of the enzyme composition. Said heating is preferably done at a temperature of at least 75° C., preferably at least 85° C., more preferably at least 90° C., such as in the range of 85 to 100° C., for example in the range of 90 to 100° C. Heating may be done for any suitable amount of time, e.g. for in the range of 15 to 120 min. such as in the range of 15 to 60 min. for example for approximately 30 min.

Thus, in one embodiment mashing may consist of incubation at a temperature 60 to 72° C. as described above followed by incubation at a temperature of at least 85° C., such as at least 90° C. as described above.

After mashing the aqueous extract is separated from the barley kernels (e.g. from the milled barley) in order to obtain either the beverage or a beverage base, which can be further processed into a beverage.

Said separation may be performed by any useful method, for example by using any of the methods for separating wort from spent grains conventionally employed in breweries. Non-limiting examples of methods for separation the aqueous extract from the barley kernels (e.g. from the milled barley) includes centrifugation, decanting, filtration or use of a lautertun.

Barley Plant

The present invention provides methods for preparing high β-glucan beverages from kernels of a barley plant. In order to arrive at beverages containing sufficiently high levels of β-glucan, which at the same time are stable and have low viscosity, it is preferable to use barley plants having high levels of β-glucans and having β-glucan characterized by a high ratio of DP3/DP4.

The barley plant may be any plant of the species *Hordeum vulgare*, including any breeding line or cultivar or variety.

Thus, the barley plants to be used with the methods of the present invention may have the following characteristics:
  i. comprises at least 10% β-glucans
  ii. have a ratio of DP3/DP4 in said β-glucan of at least 3

For beer brewing it is generally preferred to use barley plants with low levels of β-glucans, and thus typical malting varieties of barley have low levels of β-glucans. β-glucans confer viscosity to the wort, which is generally less desirable. However, the barley plants to be used with the present invention preferably have a high level of β-glucan.

Thus, it is preferred that the barley plant to be used with the methods of the invention have kernels that comprises at least 10% β-glucans, more preferably at least 11% β-glucan, even more preferably at least 12% β-glucan, such as at least 13% β-glucans, for example at least 14% β-glucans, such as at least 15% β-glucans. Said percentages are provided as % of dry matter in the kernel per weight.

In order to determine the % of β-glucans in the kernels of a barley plant, then the weight of β-glucans in the kernels is determined, and the total weight of the dry matter in the kernels is determined. The % β-glucan can then be calculated. The β-glucan contant may be determined by extracting β-glucans, e.g. by mashing as described herein above in the section "Mashing" and determining the β-glucan content in the aqueous extract. The amount of β-glucan can for example be determined using the calcofluor method. The calcofluor method is a fluorimetric method and can be performed according to Brewing EBC standards, 1994. The calcofluor dye has the capacity to bind to β-glucans present in solution and increases its fluorescence in a direct proportion with the content of β-glucan bounded.

A useful method for determining % of β-glucans in the kernels of a barley plant is outlined in Example 5a herein below.

In addition to having a high content of β-glucan it is also of importance that said barley plant contains β-glucan having a high ratio of DP3/DP4. The DP3/DP4 ratio describes the β-glucan oligomer block structure. Thus, barley β-glucan contains blocks of cellotriose and blocks of cellotetraose and the DP3/DP4 ratio describes the ratio between cellotriose blocks and cellotetraose blocks. Cellotriose is a trisaccharide in which three glucose units are joined with 1,4-βlinkages. Cellotetraose is a tetrasaccharide in which four glucose residues are joined with 1,4-βlinkages. The ratio can be determined by digesting β-glucan with lichenase and determining the amount of released DP3 and DP4 blocks. Lichenase is an enzyme catalysing hydrolysis of (1→3)-β-glucosidic linkages, which is positioned next to a (1→4)-β-glucosidic linkage. One useful method for determining the DP3/DP4 ratio is described in Example 5a.

In one embodiment the present invention involves mashing barley kernels in the presence of an enzyme composition comprising α-amylase and endo-1,3(4)-β-glucanase activity and optionally also a glucoamylase and/or pullulanase activity. The enzymes both aid in the proper extraction of β-glucan, but also aid in obtaining β-glucan with an average low molecular weight of in the range of 80 to 200 kDa. However, if the β-glucan has a low ratio of DP3/DP4, then this will typically result in more or less complete digestion of the β-glucan by the enzyme composition, and accordingly, makes it difficult to prepare beverages with a natural high β-glucan content according to the invention.

Accordingly, it is preferred that the β-glucan contained in the barley plants to be used with the invention have a high ratio of DP3/DP4. In particular, it is preferred that the kernels of the barley plant to be used contain β-glucan having a ratio of DP3/DP4 of at least 3, such as of at least 3.2. In a preferred embodiment, the kernels of the barley plant to be used contain β-glucan having a ratio of DP3/DP4 of at least 3.4, for example at least 3.6, such as at least 3.7.

In one embodiment of the invention the barley plant carries a mutation in the HvNst1 gene. Such mutations lead to a barley plant comprising at least 10% β-glucans and having a ratio of DP3/DP4 in said β-glucan of at least 3, such as at least 3.4.

In particular, it is preferred that said mutation results in reduced NST1 function, more preferably said mutation results in total loss of NST1 function. The sequence of wild-type barley NST1 is provided herein as SEQ ID NO:1. Barley NST1 is an ADP-Glc transporter, and the term "total loss of NST1 function" as used herein refers to one of the following situations:

1) The barley plant does not contain NST1 protein
2) The barley plant contains mutant NST1, wherein said mutant NST1 is not capable of transporting ADP-glucose Thus, in one embodiment of the invention the barley plant carries a mutation in the HvNst1 gene, leading to reduced expression of the NST1 protein. Thus, the barley plant may carry a mutation in the HvNst1 gene leading to expression of NST1 protein at a level at least 80% reduced compared to expression of NST1 protein in a wild type barley plant, such as in cv Quench.

In another embodiment of the invention the barley plant carries a mutation in the HvNst1 gene, wherein said mutant HvNst1 gene encodes a mutant NST1 protein with a loss of function. In particular, said mutant NST1 has a substitution of at least one amino acid compared to SEQ ID NO:1, such as a substitution of at least one conserved amino acid compared to SEQ ID NO:1. In particular, the mutant NST1 has a substitution of at least one of the amino acids marked by a black box in FIG. 10 for another amino acid.

It is also comprised within the invention that the barley plant carries a mutation in the HvNst1 gene, wherein said mutant HvNst1 gene encodes a mutant NST1 protein lacking at least one amino acid compared to SEQ ID NO:1, such as lacking at least one conserved amino acid compared to SEQ ID NO:1. In particular, the mutant NST1 lacks one or more of the amino acids marked by a black box in FIG. 10. Thus, said mutant NST1 may lack at least 10, such as at least 20, for example at least 30, such as at least 50 of the amino acids marked by a black box in FIG. 10.

In one embodiment of the invention, the barley plant carries a mutation in the HvNst1 gene, wherein said mutant HvNst1 gene encodes a mutant NST1 protein, wherein the amino acid 228 of SEQ ID NO:1 has been deleted or substituted for another amino acid. In particular, the barley plant may carry a mutation in the HvNst1 gene, wherein the mutant HvNst1 gene encodes NST1 of SEQ ID NO:1, wherein the Pro residue at position 228 has been substituted for a Ser residue.

In another embodiment of the invention, the barley plant carries a mutation in the HvNst1 gene, wherein said mutant HvNst1 gene encodes a mutant NST1 protein, wherein the amino acid amino acid 273 of SEQ ID NO:1 has been deleted or substituted for another amino acid. In particular, the barley plant may carry a mutation in the HvNst1 gene, wherein the mutant HvNst1 gene encodes NST1 of SEQ ID NO:1, wherein the Val residue at position 273 has been substituted for a Glu.

One non-limiting example of a barley plant carrying a mutation in the HvNst1 gene, wherein the mutant HvNst1 gene encodes NST1 of SEQ ID NO:1, wherein the Val residue at position 273 has been substituted for a Glu is the barley plant known as lys5f is available at the Nordic Genetic Resource Center under the accession number NGB20030.

Enzyme Composition

The present invention provides methods for preparing high β-glucan beverages from kernels of a barley plant by mashing barley kernels (e.g. milled barley) in the presence of an enzyme composition. Said enzyme composition comprises α-amylase, and endo-1,3(4)-β-glucanase activity and optionally a glucoamylase and/or pullulanase activity. One enzyme may have one or more of these activities, but in general, the enzyme composition comprises one enzyme having α-amylase activity, and one enzyme having endo-1,3(4)-β-glucanase activity and optionally one enzyme having glucoamylase activity and/or one enzyme having pullulanase activity.

In one embodiment the enzyme composition comprises α-amylase, glucoamylase and endo-1,3(4)-β-glucanase activity.

In one embodiment the enzyme composition comprises α-amylase, glucoamylase, pullulanase and endo-1,3(4)-6-glucanase activity.

The enzyme having α-amylase activity may be an α-amylase. An α-amylase according to the invention is an enzyme capable of catalyzing endohydrolysis of (1→4)-α-D-glucosidic linkages in polysaccharides containing three or more (1→4)-α-linked D-glucose units. In particular the α-amylase according to the present invention are α-amylase enzymes classified under EC 3.2.1.1.

A particular α-amylase enzyme to be used in the methods of the invention may be a *Bacillus* α-amylase. Well-known *Bacillus* α-amylases include α-amylase derived from a strain of *B. licheniformis*, *B. amyloliquefaciens*, or *B. stearothermophilus*. In one aspect of the present invention, a contemplated *Bacillus* α-amylase is an α-amylase as defined in WO 99/19467 on page 3, line 18 to page 6, line 27.

Another example of an α-amylase to be used with the present invention is the enzyme disclosed as SEQ ID NO: 3 in WO 99/19467 or a functional homologue thereof sharing at least 70%, such as at least 75%, for example at least 80%, such as at least 85%, for example at least 90%, such as at least 95%, such as at least 98% sequence identity therewith. The α-amylase may also be an α-amylase sharing at least 70%, such as at least 75%, for example at least 80%, such as at least 85%, for example at least 90%, such as at least 95%, such as at least 98% sequence identity with the amino acid sequence disclosed as SEQ ID NO: 3 in WO 99/19467 with the mutations: 1181*+G182*+N193F. Also contemplated is the α-amylase Termamyl® SC available from Novozymes A/S, Denmark. Another particular α-amylase to be used in the methods of the invention may be any fungal α-amylase, e.g., an α-amylase derived from a species within *Aspergillus*, and preferably from a strain of *Aspergillus niger*. Especially contemplated is the α-amylase shown as SEQ ID NO: 1 in WO 2002/038787 or a functional homologue thereof sharing at least 70%, such as at least 75%, for example at least 80%, such as at least 85%, for example at least 90%, such as at least 95%, such as at least 98% sequence identity therewith. In a preferred embodiment, the α-amylase is the polypeptide of SEQ ID NO:3 or a functional homologue thereof sharing at least 70%, such as at least 75%, for example at least 80%, such as at least 85%, for example at least 90%, such as at least 95%, such as at least 98% sequence identity therewith.

The amount of α-amylase to be added depends on various parameters and is generally known to the person skilled in the art. In one aspect, the α-amylase activity in the mash is 0.1-1.0 KNU/g, more preferably 0.2-0.4 KNU/g, and most preferably 0.25-0.35 KNU/g dry weight barley. In another aspect the α-amylase activity in the mash is at least 0.1 KNU/g, such as at least 0.2-0.4 KNU/g, for example at least 0.25 KNU/g dry weight barley. In another aspect the α-amylase activity in the mash is in the range of 0.1 to 10 KNU/g, such as in the range of 0.1 to 5 KNU/g, for example in the range of at least 0.2 to 5 KNU/g dry weight barley. One Kilo Novozymes α-amylase Unit (KNU) equals 1000 NU. One KNU is defined as the amount of enzyme which, under standard conditions (i.e. at 37° C.+/−0.05; 0.0003 M Ca2+; and pH 5.6) dextrinizes 5.26 g starch dry substance Merck Amylum solubile.

A functional homologue of an α-amylase is an enzyme, which can catalyze endohydrolysis of (1→4)-α-D-glucosidic linkages in polysaccharides containing three or more (1→4)-α-linked D-glucose units.

The enzyme having glucoamylase activity may be any glucoamylase, but in general it is an enzyme having glucan 1,4-α-glucosidase activity. In particular the glucoamylase may be an enzyme catalyzing hydrolysis of terminal (1→4)-linked α-D-glucose residues successively from non-reducing ends of the chains with release of β-D-glucose. In particular the glucoamylase according to the present invention are α-amylase enzymes classified under EC 3.2.1.3.

One example of a glucoamylases is Uniprot: B0CVJ1, which discloses a polypeptide from Laccaria bicolor. Other examples are the glucoamylases from Trametes cingulata described in WO2006/069289.

The glucoamylase may also be a glucoamylase from the fungus Gloeophyllum, e.g. from G. abietinum, G. sepiarium, or G. trabeum. Such glucoamylases may for example be a polypeptide comprising an amino acid sequence having preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, even more preferably at least 93%, most preferably at least 94%, and even most preferably at least 95%, such as at least 96%, at least 97%, at least 98%, at least 99% or even 100% identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18 of WO2011068803.

The glucoamylase may also be glucoamylase from Penicillium oxalicum, e.g. those disclosed by Yoshiki YAMASAKI, Agric. Biol. Chem., 41 (5), 755-762, 1977)—The glucoamylase may also b a polypeptide comprising an amino acid sequence having preferably at least 61.5%, more preferably at least 63%, more preferably at least 65%, more preferably at least 68%, more preferably at least 70%, more preferably at least 75%, more preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, 97%, 98%, 99% or 100% identity to the mature polypeptide of SEQ ID NO: 2 of WO2011127802, The enzyme having pullulanase activity may be any pullulanase. Pullulanase is preferably an enzyme capable of catalyzing hydrolysis of α-(1→6)-D-glucosidic linkages in pullulan, amylopectin and glycogen. Pullulan is a linear polymer of 1→6-linked maltotriose units. Pullulanase according to the present invention are preferably pullulanases classified under EC 3.2.1.41.

The pullulanase according to the present invention may be pullulanase from e.g. *Pyrococcus* or *Bacillus*, such as *Bacillus acidopullulyticus* e.g. the one described in Kelly et al., 1994, FEMS Microbial. Letters 115: 97-106, or a pullulanase available from Novozymes A/S as Promozyme 400 L. The pullulanase may also be from *Bacillus naganoencis*, or *Bacillus deramificans* e.g. such as derived from *Bacillus deramificans* (U.S. Pat. No. 5,736,375). The pullulanase may also be an engineered pullulanases from, e.g. a *Bacillus* strain. The pullulanase may also be the pullulanase available from Novozymes NS, Denmark, as Attenuzyme® Flex. Other pullulanases may be derived from *Pyrococcus woesei* described in PCT/DK91/00219, or the pullulanase may be derived from *Fervidobacterium* sp. *Ven* described in PCT/DK92/00079, or the pullulanase may be derived from *Thermococcus celer* described in PCT/DK95/00097, or the pullulanase may be derived from *Pyrodictium abyssei* described in PCT/DK95/00211, or the pullulanase may be derived from *FetVidobacterium* pennavorans described in PCT/DK95/00095, or the pullulanase may be derived from *Desulforococcus mucosus* described in PCT/DK95/00098.

Most preferably the pullulanase is derived from *Bacillus acidopullulyticus*. A preferred pullulanase enzyme to be used with the methods of the invention is the polypeptide of SEQ ID NO:4 or a functional homologue thereof sharing at least 70%, such as at least 75%, for example at least 80%, such as at elast 85%, for example at least 90%, such as at least 95%, such as at least 98% sequence identity therewith.

The pullulanase may be added in effective amounts well known to the person skilled in the art. In one aspect, the pullulanase is added in dosage of 0.1 to 3 PUN/g barley dry matter, such as 0.2 to 2.9, such as 0.3 to 2.8, such as 0.3 to 2.7 such as 0.3 to 2.6 such as 0.3 to 2.5 such as 0.3 to 2.4, such as 0.3 to 2.3, such as 0.3 to 2.2, such as 0.3 to 2.1, such as 0.3 to 2.0, such as 0.3 to 1.9, such as 0.3 to 1.8, such as 0.3 to 1.7, such as 0.3 to 1.6, most preferably pullulanase is added in dosage such as 0.3 to 1.5, preferably 0.4 to 1.4, more preferably 0.5 to 1.3, more preferably 0.6 to 1.2, more preferably 0.7 to 1.1, more preferably 0.8 to 1.0, more preferably 0.9 to 1.0. In a particular embodiment of the invention the enzyme is added in approximately 0.3 PUN/g barley dry matter, such as approximately 0.4 PUN/g barley dry matter, such as approximately 0.5 PUN/g barley dry matter.

One pullulanase unit (PUN) is the amount of enzyme which, under standard conditions (i.e. after 30 minutes reaction time at 40° C. and pH 5.0; and with 0.2% pullulan as substrate) hydrolyzes pullulan, liberating reducing carbohydrate with a reducing power equivalent to 1 micromol glucose per minute. Pullulanase activity is by measured by detection of increased reducing sugar capacity.

A functional homologue of the polypeptide of SEQ ID NO:4 is an enzyme, which can catalyze hydrolysis of α-(1→6)-D-glucosidic linkages in pullulan, amylopectin and glycogen.

The enzyme having endo-1,3(4)-β-glucanase activity may be any endo-1,3(4)-β-glucanase. Endo-1,3(4)-β-glucanase is preferably an enzyme capable of catalyzing endohydrolysis of (1→3)- or (1→4)-linkages in β-glucans when the glucose residue whose reducing group is involved in the linkage to be hydrolyzed is itself substituted at C-3.

In one embodiment of the invention the endo-1,3(4)-β-glucanase according to the present invention is an enzyme endo-1,3-1,4-β-D-glucanase. In a preferred embodiment of the invention the endo-1,3(4)-β-glucanase is a lichenase, preferably a lichenase classified under EC 3.2.1.73.

The endo-1,3(4)-β-glucanase may be derived from any suitable organism, for example the endo-1,3(4)-β-glucanase may be lichenase from *Bacillus subtilis*. For example the endo-1,3(4)-β-glucanase may be the polypeptide of SEQ ID NO:5 or a functional homologue thereof sharing at least 70%, such as at least 75%, for example at least 80%, such as at elast 85%, for example at least 90%, such as at least 95%, such as at least 98% sequence identity therewith.

Figure 2:
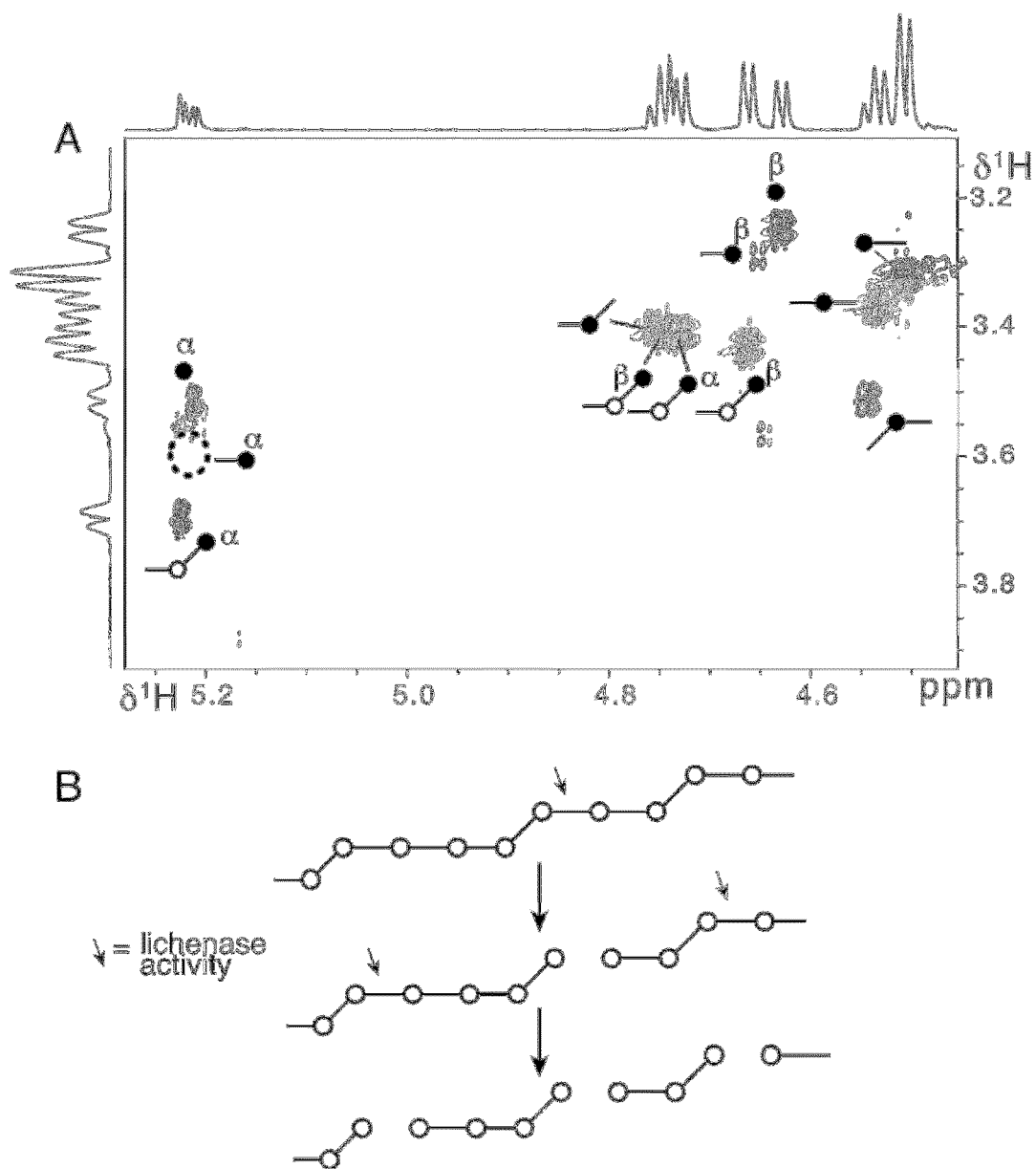
FIG. 2: $^1$H-$^1$H COSY spectrum of lys5f β-glucan extracted with Termamyl® SC partially degraded by the Attenuzyme® Flex lichenase side activity at 65° C.
Figure 4:
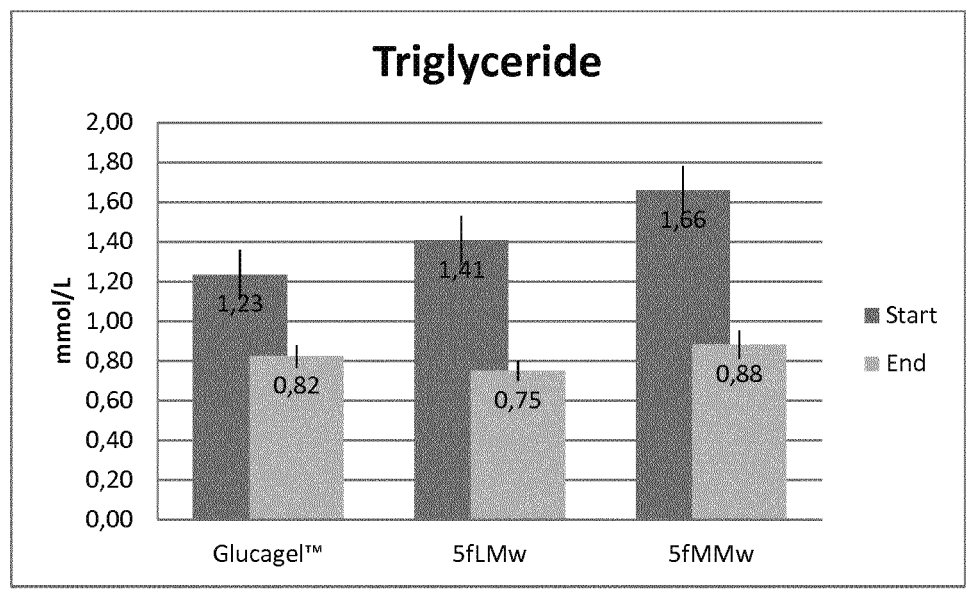
FIG. 4: changes from baseline in triglyceride (mmol/L) after 4 weeks β-glucan treatments in rats. Mean values±SEM n=12 per treatment.
Figure 5:
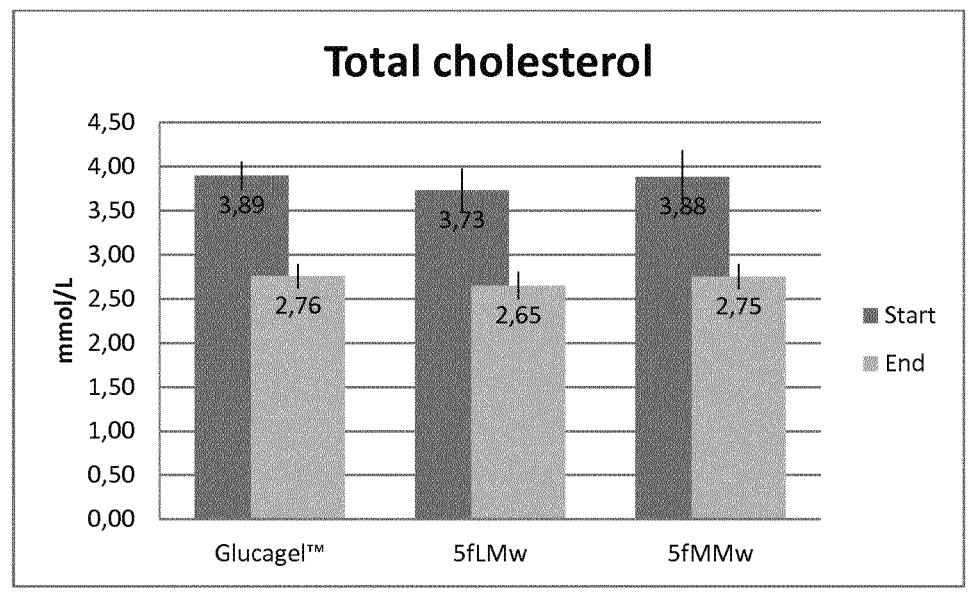
FIG. 5: changes from baseline in total cholesterol (mmol/L) after 4 weeks β-glucan treatments in rats. Mean values±SEM n=12 per treatment
Figure 6:
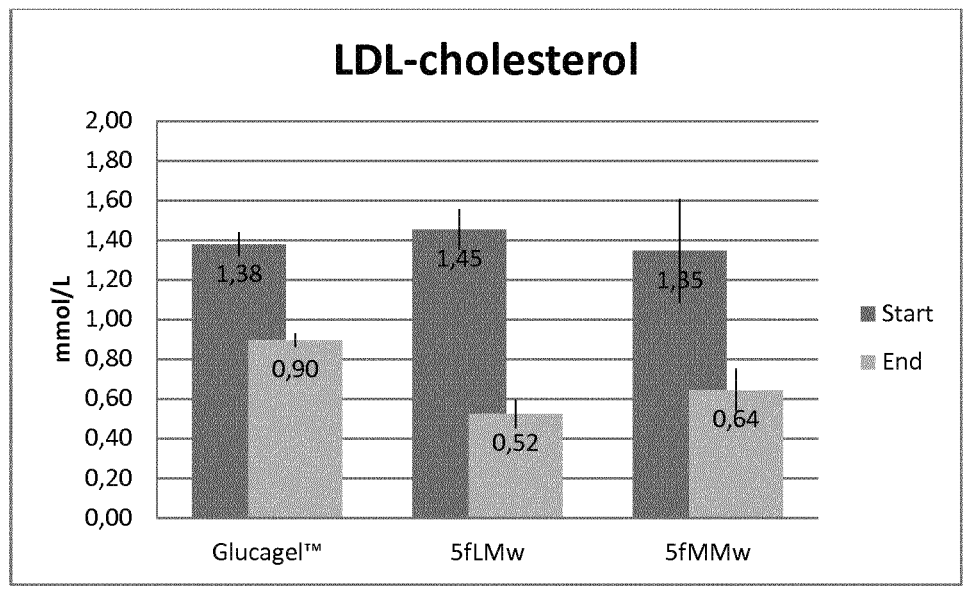
FIG. 6: changes from baseline in LDL-cholesterol (mmol/L) after 4 weeks β-glucan treatments in rats. Mean values±SEM n=12 per treatment
Figure 7:
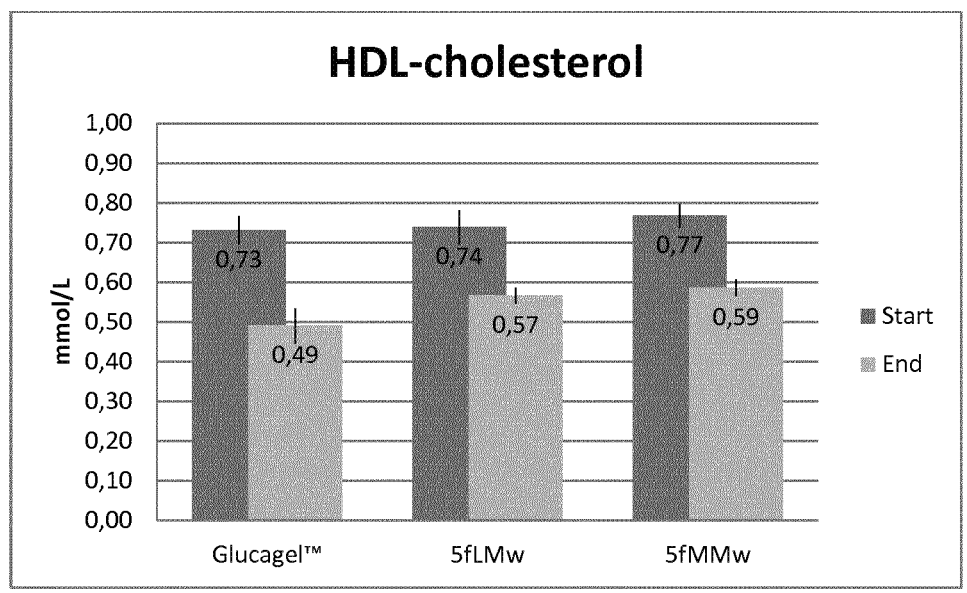
FIG. 7: changes from baseline in HDL-cholesterol (mmol/L) after 4 weeks β-glucan treatments in rats. Mean values±SEM n=12 per treatment

In another embodiment the endo-1,3(4)-β-glucanase may be the lichenase encoded by the GluB gene of *Bacillus polymyxa* or a functional homologue thereof sharing at least 70%, such as at least 75%, for example at least 80%, such as at elast 85%, for example at least 90%, such as at least 95%, such as at least 98% sequence identity therewith. The sequence of the lichenase encoded by the GluB gene of *Bacillus polymyxa* is shown in FIG. 2 of Gosalbes et al., JOURNAL OF BACTERIOLOGY, December 1991, Vol. 173, No. 23, p. 7705-7710.

In another embodiment the endo-1,3(4)β-glucanase may be any of the lichenases described in U.S. Pat. No. 6,103, 511, in particular the endo-1,3(4)β-glucanase may be the polypeptide shown as SEQ ID NO:2 in U.S. Pat. No. 6,103,511 or a functional homologue thereof sharing at least 70%, such as at least 75%, for example at least 80%, such as at least 85%, for example at least 90%, such as at least 95%, such as at least 98% sequence identity therewith.

In one embodiment the endo-1,3(4)β-glucanase may be a β-glucanase classified under E.C. 3.2.1.4. The β-glucanase may be of microbial origin, such as derivable from a strain of a bacteria (e.g. *Bacillus*) or from a filamentous fungus (e.g., *Aspergillus, Trichoderma, Humicola, Fusarium*). Preferred are beta-glucanases derived from *Trichoderma* sp., *T. reesei* or *T. viride*. The endo-1,3(4)β-glucanase may in particular be a polypeptide of any of the sequences shown as SEQ ID NO: 6, SEQ ID NO:7 or SEQ ID NO:8 in WO2006/066582 or a functional homologue thereof sharing at least 70%, such as at least 75%, for example at least 80%, such as at least 85%, for example at least 90%, such as at least 95%, such as at least 98% sequence identity therewith.

Commercially available beta-glucanase preparations which may be used include CELLUCLAST®), CELLUZYME®, CEREFLO® and ULTRAFLO® (available from Novozymes A/S), GC 880, LAMINEX™ and SPEZYME® CP (available from Genencor Int.) and ROHAMENT® 7069 W (available from Röhm, Germany).

In one embodiment the endo-1,3(4)β-glucanase is an endoglucanase derived from *Humicola* sp., such as the endoglucanase from *Humicola insolens*, the endoglucanase from *H. insolens* or from *Thermoascus* sp., such as the endoglucanase derived from *Thermoascus aurantiacus*, or from *Aspergillus* sp., such as the endoglucanase derived from *Aspergillus aculeatus*, or from *Trichoderma* sp. preferably from *T. reesei* and/or *T. viride*, such as the family 5 endoglucanase, the family 7, beta-glucanase or the fam 12, beta-glucanase. The endo-1,3(4)β-glucanase may in particular be a polypeptide of any of the sequences shown as SEQ ID NO: 3, SEQ ID NO:4, SEQ ID NO:6, SEQ ID NO:16, SEQ ID N018, SEQ ID NO:19 or SEQ ID NO:20 in WO2005/059084 or a functional homologue thereof sharing at least 70%, such as at least 75%, for example at least 80%, such as at least 85%, for example at least 90%, such as at least 95%, such as at least 98% sequence identity therewith.

A functional homologue of an endo-1,3(4)-β-glucanase e.g. the polypeptide of SEQ ID NO:5 is an enzyme, which can catalyze endohydrolysis of (1→3)- or (1→4)-linkages in β-glucans when the glucose residue whose reducing group is involved in the linkage to be hydrolyzed is itself substituted at C-3.

The amount of endo-1,3(4)-β-glucanase to be added may depend on various parameters. In general, an amount of β-glucanase is added, which results in β-glucans having an average Mw of in the range of 80 to 200 kDa after mashing. It is generally preferred that only relatively small amounts of endo-1,3(4)-β-glucanase is applied. Thus, in one embodiment, the endo-1,3(4)-β-glucanase activity in the mash is at the most 0.5 EGU/g, and most preferably at the most 0.3 EGU/g dry weight barley, even more preferably at the most 0.1 EGU/g, for example at the most 0.05 EGU/g, such as at the most 0.03 EGU/g. In another aspect the endo-1,3(4)-β-glucanase activity in the mash is in the range of 0.0005 to 0.5 EGU/g, preferably in the range of 0.005 to 0.3 EGU/g, such as in the range of 0.001 to 0.1 EGU/g, for example in the range of at least 0.001 to 0.05 EGU/g dry weight barley. The endo-1,3(4)-β-glucanase activity may be measured in endoglucanase units (EGU), determined at pH 6.0 with carboxymethyl cellulose (CMC) as substrate as follows. A substrate solution is prepared, containing 34.0 g/l CMC (Hercules 7 LFD) in 0.1 M phosphate buffer at pH 6.0. The enzyme sample to be analyzed is dissolved in the same buffer. 5 ml substrate solution and 0.15 ml enzyme solution are mixed and transferred to a vibration viscosimeter (e.g. MIVI 3000 from Sofraser, France), thermostated at 40° C. for 30 minutes. One EGU is defined as the amount of enzyme that reduces the viscosity to one half under these conditions.

As used herein the term "X in the mash" refers to the amount of X present during mashing (e.g. during step b) of the methods described herein). Enzyme activity in the mash may be indicated as units per g dry barley present during mashing.

In one preferred embodiment of the invention the enzyme composition comprises Attenuzyme® Flex available from Novozymes, Denmark. In particular, the enzyme composition may comprise or even consist of a mixture of Termamyl® SC and Attenuzyme® Flex, both available from Novozymes, Denmark.

Processing Beverage Base into a Beverage

The present invention relates to methods for preparing a beverage, said methods involving mashing a barley kernels in the presence of an enzyme composition and separating the aqueous extract from the barley kernels (e.g. the milled barley).

Said aqueous extract may constitute the beverage. However, frequently, the aqueous extract is a beverage base, which is further processed before arriving at the final beverage.

The beverage base is frequently subjected to a step of heating to a temperature of at least 75° C. This may have several effects including pasteurizing the beverage. Said heating is preferably done at a temperature of at least 75° C., preferably at least 85° C., more preferably at least 90° C., such as in the range of 85 to 100° C., for example in the range of 90 to 100° C. Heating may be done for any suitable amount of time, e.g. for in the range of 15 to 120 min. such as in the range of 15 to 60 min. for example for approximately 30 min. Thus, the beverage according to the invention may be a pasteurized beverage.

The beverage base may also be subjected to ultra-high temperature processing (UHT) by pre-heating to between 70-80° C. followed by heating to above 90° C. for a short period of time, e.g. for 1 to 5 seconds, such as for 1 to 2 seconds or 4- to 5 seconds.

The beverage base may also be subjected to a homogenization treatment, e.g. treatment at 100-200 bar.

Frequently, step d) comprises adding one or more additional compounds and/or one or more additional liquids to the beverage base obtained in step c) in order to produce a beverage. In such cases above-mentioned heat treatment or UHT may be performed before or after adding said additional compounds and/or additional liquids.

The methods of the invention may comprise a step of adding one or more additional compound(s). The additional compound may for example be a flavor compound, a preservative or a functional ingredient. The additional compound may also be a color, a sweetener, a pH regulating agent or a salt. The sweetener may for example be an artificial sweetener, a low calorie sweetener or sugar. The pH regulating agent may for example be a buffer or an acid, such as lactic acid or citric acid.

Functional ingredients may be any ingredient added to obtain a given function. Preferably a functional ingredient renders the beverage healthier. Non-limiting examples of functional ingredients includes soluble fibres, proteins, added vitamins or minerals.

The preservative may be any food grade preservative, for example it may be benzoic acid, sorbic acid, sorbates (e.g. potassium sorbate), sulphites and/or salts thereof.

The additional compound may also be $CO_2$. In particular, $CO_2$ may be added to obtain a carbonated beverage.

The flavour compound to be used with the present invention may be any useful flavour compound. The flavour compound may for example be selected from the group consisting of aromas, plant extracts, plant concentrates, plant parts and herbal infusions.

Thus, the flavour compound may for example be an aroma. Aromas are typically organic compounds, for example they may be plant secondary metabolites. The aroma may be any aroma, for example a fruit aroma or vanilla aroma.

The plant extract may for example be a herbal extract. Non-limiting examples of herbal extracts includes an extract of green tea, black tea, rooibos, peppermint or hops. The plant extract may also be a flower extract. Non limiting examples of flower extracts include hibiscus, camomile, elderflower, lavender or linden flower.

The plant extract may also be a fruit extract. Plant parts may for example be dried or fresh herbs, such as hops pellets, dried of fresh flowers or fruits.

The plant concentrate may be a fruit concentrate, for example a fruit juice, which has been concentrated by removal of water.

Non-limiting examples of fruits useful for fruit aroma, fruit extract or fruit concentrates include orange, apple, banana, lemon, passion fruit, mango, pineapple, pears, kumquats or pomelo, The flavor compound may also be quinine, for example in embodiments where the beverage is a tonic like beverage.

At least one additional compound may also be a stabilizer. Said stabilizer may for example be any ingredient capable of stabilizing the soluble β-glucans, e.g. capable of stabilizing the soluble β-glucans in an elastic gelling matrix. Said stabilizer may for example be a gellan gum, such as Kelcogel® LT-100 available from CP Kelco, Denmark. Said stabilizer may be added to the beverage in any suitable amount, such as to a final concentration of in the range of 0.001 to 0.1% (w/w), for example to a final concentration of in the range of 0.01 to 0.05% (w/w).

The additional liquid may be water. The additional liquid may also be another beverage, for example a fruit juice, a syrup, a carbonated soft drink or a beer. In particular the additional liquid may be a fruit juice.

The step d) may also comprise fermenting the beverage base with one or more microorganisms. In particular, the beverage base may be fermented with yeast in order to produce an alcoholic beverage. Said yeast may be any yeast, e.g. *S. cerevisiae* or *S. pastorianus*. Said microorganisms may also be bacteria, for example *Lactobacillus*, such as *L. lactis*. For example the beverage base may be fermented in a similar manner as conventional wort is fermented during beer production. Thus any convention method for producing beer may be employed, wherein the conventional wort is exchanged for the beverage base prepared by the methods of the invention.

Clinical Conditions

Interestingly, it has been demonstrated that the β-glucans prepared according to the methods of the invention are useful for reducing both LDL and total cholesterol. Accordingly, the beverages produced by the present invention are useful for reducing the risk of several clinical conditions associated with increased levels of LDL and cholesterol.

Thus, in one aspect the invention relates to a beverage containing at least 2 g/L β-glucans, wherein said β-glucans have an average molecular weight in the range of 80 to 200 kDa, wherein the beverage is for reducing the risk of acquiring a clinical condition in an individual in need thereof, wherein the clinical condition is selected from the group consisting of coronary heart disease, and diabetes.

The invention also provides methods for reducing the risk of acquiring a clinical condition in an individual in need thereof, wherein the clinical condition is selected from the group consisting of coronary heart disease, diabetes and infections, said method comprising administering a beverage containing at least 2 g/L β-glucans, wherein said β-glucans have an average molecular weight in the range of 80 to 200 kDa to said individual in an effective amount.

It is preferred that said individual has an intake of the beverages of the invention, which is sufficient to allow a daily intake of at least 2 g β-glucans, such as at least 3 g β-glucans, for example in the range of 3 to 50 g β-glucans, such as in the range of 3 to 20 g β-glucans, for example in the range of 3 to 10 g β-glucans. It may also be preferred that the individual has an intake of in the range of 0.5 to 2 g, such as in the range of 0.5 to 1.5 g, for example approximately 1 g, such as 1 g β-glucans per serving. In the context of the beverages of the present invention, then a serving is typically in the range of 250 to 330 ml, for example approximately 250 ml and/or approximately 330 ml.

Thus, said effective amount may be at least 2 g β-glucans, such as at least 3 g β-glucans, for example in the range of 3 to 50 g β-glucans, such as in the range of 3 to 20 g β-glucans, for example in the range of 3 to 10 g β-glucan per day.

The invention further provides a method for reducing blood levels of at least one lipid selected from the group consisting of triglycerides, cholesterol, and LDL in an individual in need thereof, wherein said method comprises intake of the beverage of the invention containing at least 2 g β-glucans, such as at least 3 g β-glucans, for example in the range of 3 to 50 g β-glucans, such as in the range of 3 to 20 g β-glucans, for example in the range of 3 to 10 g β-gluca according to any one of claims 29 to 31 by said individual.

It is also an object of the invention to provide methods for reducing the risk of obesity in an individual in need thereof. The methods involve intake of the beverages of the invention containing at least 2 g/L β-glucans, wherein said β-glucans have an average molecular weight in the range of 80 to 200 kDa by said individual in an effective amount. The effective amount is preferably the effective amount indicated above.

It is also an object of the invention to provide methods for reducing obesity in an individual in need thereof. The methods involve intake of the beverages of the invention containing at least 2 g/L β-glucans, wherein said β-glucans have an average molecular weight in the range of 80 to 200 kDa by said individual in an effective amount. The effective amount is preferably the effective amount indicated above.

Said individual is preferably a human being. In some embodiments of the invention the individual is an obese human being.

| Sequence listing | | |
|---|---|---|
| SEQ ID NO: 1 | Protein sequence of NST1 of barley | Gene bank accession AY560327 |
| SEQ ID NO: 2 | DNA sequence of barley Hv.Nst1 gene | |
| SEQ ID NO: 3 | Protein sequence of α-amylase of Bacillus stearothermophilus | |

| Sequence listing | | |
|---|---|---|
| SEQ ID NO: 4 | Protein sequence of pullulanase of Bacillus acidopullulyticus | |
| SEQ ID NO: 5 | Protein sequence of lichenase of Bacillus subtilis | Gene Bank accession Z46862.1 |

Items

The invention may further be defined by the following items:

1. A method for preparing a beverage comprising at least 2 g/L β-glucan, wherein said β-glucans have an average molecular weight in the range of 80 to 200 kDa, said method comprising the steps of
  a) providing kernels of a barley plant, wherein said kernels have the following characteristics:
    i. comprising at least 10% β-glucans
    ii. having a ratio of DP3/DP4 in said β-glucan of at least 3
  b) mashing said kernels with water in the presence of an enzyme composition, wherein said composition comprise α-amylase, and endo-1,3(4)-β-glucanase activity, thereby obtaining an aqueous extract
  c) separating said aqueous extract from the barley kernels, thereby obtaining a beverage or a beverage base
  d) optionally processing the beverage base into a beverage.

2. The method according to item 1, wherein the enzyme composition further comprises a glucoamylase activity.

3. The method according to any one of the preceding items, wherein the enzyme composition further comprises a pullulanase activity.

4. The method according to any one of the preceding items, wherein the beverage comprises at least 3 g/L, such as at least 4 g/L β-glucans.

5. The method according to any one of the preceding items, wherein said kernels comprise at least 11%, such as at least 12% β-glucans.

6. The method according to any one of the preceding items, wherein the ratio of DP3/DP4 in said β-glucan is at least 3.2, such as at least 3.4, for example at least 3.6, such as at least 3.7.

7. The method according to any one of the preceding items, wherein the barley plant carries a mutation in the HvNst1 gene.

8. The method according to any one of the preceding items, wherein the barley plant carries a mutation in the HvNst1 gene leading to a total loss-of-function of NST1.

9. The method according to any one of items 7 to 8, wherein the mutation leads to a mutated HvNst1 gene encoding a mutated NST1 having a substitution of at least one amino acid compared to SEQ ID NO:1, wherein the amino acid for example is selected from amino acid 228 and amino acid 273 of SEQ ID NO:1.

10. The method according to any one of the preceding items, wherein the barley plant carries a mutation in the HvNst1 gene, wherein the mutant HvNst1 gene encodes NST1 of SEQ ID NO:1, wherein the Pro residue at position 228 has been substituted for a Ser residue.

11. The method according to any one of items 1 to 10, wherein the barley plant carries a mutation in the HvNst1 gene, wherein the mutant HvNst1 gene encodes NST1 of SEQ ID NO:1, wherein the Val residue at position 273 has been substituted for a Glu.

12. The method according to any one of the preceding items, wherein the barley plant carries a mutation in the HvNst1 gene leading to expression of NST1 protein at a level at least 80% reduced compared to expression of NST1 protein in a wild type barley plant, such as in cv Quench.

13. The method according to any one of the preceding items, wherein step b) comprises mixing milled barley kernels with water.

14. The method according to any one of the preceding items, wherein step b) comprises mixing milled barley kernels with water at a ratio of water to milled barley of 1 to in the range of 10 to 20.

15. The method according to any one of the preceding items, wherein the mashing of step b) comprises incubation at a temperature in the range of 60 to 72° C. 16. The method according to any one of the preceding items, wherein the mashing of step b) comprises incubation at a temperature in the range of 60 to 72° C. for in the range of 30 to 60 min.

17. The method according to any one of the preceding items, wherein said α-amylase is an enzyme classified under EC 3.2.1.1.

18. The method according to any one of the preceding items, wherein said α-amylase is polypeptide of SEQ ID NO:3 or a functional homologue thereof sharing at least 70% sequence identity therewith.

19. The method according to any one of items 2 to 18, wherein the glucoamylase is an enzyme classified under EC 3.2.1.3.

20. The method according to any one of items 3 to 19, wherein said pullulanase is an enzyme classified under EC 3.2.1.41.

21. The method according to any one of items 3 to 20, wherein said pullulanase is polypeptide of SEQ ID NO:4 or a functional homologue thereof sharing at least 70% sequence identity therewith.

22. The method according to any one of the preceding items, wherein said endo-1,3(4)-β-glucanase is a lichenase.

23. The method according to any one of the preceding items, wherein said endo-1,3(4)-β-glucanase is an enzyme classified under EC 3.2.1.73.

24. The method according to any one of the preceding items, wherein said endo-1,3(4)-β-glucanase is polypeptide of SEQ ID NO:5 or a functional homologue thereof sharing at least 70% sequence identity therewith.

25. The method according to any one of the preceding items, wherein said endo-1,3(4)-β-glucanase is an enzyme classified under E.C.3.2.1.4.

26. The method according to any one of the preceding items, wherein the endo-1,3(4)-β-glucanase activity present during mashing is at the most 0.5 EGU per g barley (dry weight), preferably at the most 0.1 EGU per g barley (dry weight).

27. The method according to any one of the preceding items, wherein the endo-1,3(4)-β-glucanase activity present during mashing is at the most 0.05 EGU per g barley (dry weight).

28. The method according to any one of the preceding items, wherein the method comprises a step of inactivating the enzyme composition for example by incubation at a temperature above 75° C.

29. The method according to any one of the preceding items, wherein the aqueous extract obtained in step c) constitutes the beverage.

30. The method according to any one of the preceding items, wherein step d) comprises heating the beverage base to a temperature of at least 75° C.

31. The method according to any one of the preceding items, wherein the step d) comprises adding one or more additional compounds and/or one or more additional liquids to the beverage base obtained in step c) in order to produce a beverage.

32. The method according to item 31, wherein at least one additional compound is selected from the group consisting of a flavor compound, a preservative and a functional ingredient.

33. The method according to any one of items 31 to 32, wherein at least one additional liquid is selected from the group consisting of fruit juice, water, and beer.

34. The method according to any one of items 31 to 33, wherein at least one additional compound is a stabilizer.

35. The method according to any one of the preceding items, wherein step d) comprises fermenting the beverage base with one or more microorganisms.

36. The method according to any one of the preceding items, wherein step d) comprises fermenting the beverage base with yeast in order to produce an alcoholic beverage.

37. The method according to any one of the preceding items, wherein the beverage has a viscosity of at the most 55 mPas.

38. The method according to any one of the preceding items, wherein the beverage has a viscosity of at the most 50 mPas, such as of the most 40 mPas, for example at the most 35 mPas.

39. The method according to any one of the preceding items, wherein the beverage has a viscosity of at the most 35 mPas.

40. A beverage comprising at least 2 g/L β-glucans, wherein said β-glucans have an average molecular weight in the range of 80 to 200 kDa and wherein said beverage is produced by the method according to any one of the preceding items.

41. The beverage according to item 40, wherein the beverage comprises at least 3 g/L, such as at least 4 g/L β-glucans.

42. The beverage according to any one of items 40 to 41, wherein the beverage has a viscosity of at the most 50 mPas, such as of the most 40 mPas, for example at the most 35 mPas.

43. A beverage according to any one of items 40 to 42, wherein the beverage is for reducing the risk of acquiring a clinical condition in an individual in need thereof, wherein the clinical condition is selected from the group consisting of coronary heart disease, and diabetes.

44. A method for reducing the risk of acquiring a clinical condition in an individual in need thereof, wherein the clinical condition is selected from the group consisting of coronary heart disease, diabetes and infections, said method comprising administering the beverage according to any one of items 40 to 42 to said individual in an effective amount.

45. A method for reducing blood levels of at least one lipid selected from the group consisting of triglycerides, cholesterol, and LDL in an individual in need thereof, wherein said method comprises intake of the beverage according to any one of items 40 to 42 by said individual.

46. A method for reducing the risk of obesity or reducing obesity in an individual in need thereof, said method comprising intake by said individual of the beverage according to any one of items 40 to 42.

47. The method according to any one of items 434 to 46, wherein the individual is a human being.

48. The method according to any one of items 44 to 47, wherein said individual is administered beverage comprising at least 3 g β-glucan daily.

EXAMPLES

The invention is further illustrated by the following examples, which should not be construed as limiting of the invention.

Example 1

Production of High β-Glucan Wort

Production of high β-glucan wort was performed on a Lochner electronic mashing device with 8 beakers. The high β-glucan wort contained >8 g/l. In this example barley of the variety lys5f was used. Lys5f is available at the Nordic Genetic Resource Center under the accession number NGB20030. Barley grains were milled on an EBC mill (adjusted to 0.5 mm). Water:flour ratio was 1:15 per weight, which is equivalent to 27 g (dry weight) barley flour mashed-in with 400 mL standard brewing water at 65° C. in a 500 ml metal beaker. Just after mixing milled barley with water, two commercial enzyme preparations (0.2% concentration/wet weight-corresponding to 400 µl of each enzyme preparation) together containing α-amylase, α-1,4 glucosidase, pullulanase and β-glucanase activity was added in order to facilitate starch dextrinification and β-glucan extraction. Two different enzyme mixtures were used, either a mixture of Termamyl® SC and Attenuzyme® Flex (TAF), or a mixture of Termamyl® SC and Attenuzyme® (TA). All enzymes were purchased from Novozymes, Denmark. Termamyl® SC comprises an α-amylase activity of 120 KNU/g, and accordingly approximately 48 KNU α-amylase per 27 g barley was used (corresponding to 1.8 KNU per g barley—dry weight). At this stage pH was adjusted to 5.5 by addition of phosphoric acid. After 45 min at 65° C., the temperature was gradually increased to 90° C. during a 25 min period, and finally kept at 90° C. for 30 min. The mash was centrifuged at 3500 rpm (RC5C) for 10 min to remove insoluble spent grain material. A total amount of 340 ml wort was poured in blue cap bottles and boiled at 90° C. for 30 min. Quantification of β-glucan was measured to be 8.4 g/L for the lys5f TAF wort wort by calcofluor (Brewing EBC standards,1994)(β-glucan Carlsberg system 5700 Analyzer, Tecator, Sweden). After boiling a commercial gellan gum stabilizing ingredient (Kelcogel® LT-100, CP Kelco, Lille Skensved, Denmark) was added to the wort in order to stabilize the soluble β-glucans in a soft and elastic gelling matrix. Final concentration of added stabilizer was 0.025%. The high β-glucan wort was kept at 5° C. until further debrewing and flavoring steps.

Example 2

Production of β-Glucan Wort

Performed essentially as described in Example 1 except wort was produced in pilot scale (500 L scale) with application of a decanter (with feed flow 700 L/h) following a centrifuge (475 Uh, back pressure of 3 bar) to separate insoluble barley material. The wort yield was 85% of the initial water input, and β-glucan was measured by calcofluor to be 4 g/L. The wort was filled into food grade containers, added potassium sorbate (25 mg/L), pH was further adjusted to 4.0 with a citric/lactic acid solution, and kept at 5° C. until stabilizing and flavoring process. Ingredients consisting of 5% sugar, 0.3% flavor, 0.1% color and 0.025% gellan gum was dispersed in the high β-glucan base at ambient temperature using high shear lab mixer followed by 5 min low speed, and allowing time for hydration for 15 min. After mixing ingredients the beverage underwent UHT and homogenization treatment to secure stability. First step was preheating to 80° C., homogenize at 180 bar following UHT at 90° C. for 4 seconds. Then cooled down to 20° C. and filled in sterile PET bottles (250 ml).

Example 3

Performed essentially as described in Example 1 except wort was produced in pilot scale with application of brewing kettles. The barley used was also lys5f, however harvested in a different growing season. After mashing the liquid was pumped to the lautertun and temperature lowered to 75° C. and left to settle for 24 h to remove insoluble barley material. A total amount of 160 L wort was transferred to wort kettle and boiled at 90° C. for 30 min. Quantification of β-glucan was measured by calcofluor to be 6 g/L of the wort.

Example 4

Description of β-Glucanase Side Activity of the Enzymes Applied in Examples 1, 2, and 3

The presence of β-glucanase side activities in the three different commercial enzyme mixtures applied in the wort production was probed on medium viscosity barley β-glucan (200 kDa) from Megazyme (Ireland). The β-glucan was dissolved by gentle heating and whirl mixing to concentrations of 1 mg in 600 µl of 50 mM potassium phosphate buffer in $D_2O$ (Cambridge Isotope Laboratories, Andover, Mass., USA), pH 6. Three substrate samples were made that way and mixed with 0.5 µl of enzyme solution (Termamyl® SC, Attenuzyme®, or Attenuzyme® Flex, respecitively). Reactions were followed in situ by high resolution nuclear magnetic resonance (NMR) spectroscopy for 240 min at 18° C. FIG. 1 shows the end products of β-glucan degradation by Attenuzyme® Flex, Attenuzyme® and Termamyl® SC at 18° C. The highest β-glucanase side activity was found in Attenuzyme® Flex (FIG. 1) followed by Attenuzyme®. No β-glucanase activity was observed in Termamyl® SC. Enzyme activity was judged by the emergence of reducing end signals other than glucose (present in the enzyme mixtures), as indicated in FIG. 2, which shows $^1H$-$^1H$ COSY spectrum of lys5f β-glucan degraded by the Attenuzyme® Flex β-glucanase (lichenase) side activity at 65° C.

The site-specific action of the β-glucanase activity was investigated using a lys5f β-glucan sample extracted solely by Termamyl® SC under real process conditions (as described in Example 1), i.e. at 65° C. Homonuclear $^1H$-$^1H$ DQF COSY spectra were recorded on enzyme-degraded samples using a 800 MHz Bruker (Fällanden, Switzerland) NMR spectrometer equipped with a TCI cryoprobe and 18.7 T magnet (Oxford Magnet Technology, Oxford, UK) and were used to identify β-glucans formed by exposure to the Attenuzyme® Flex enzyme mixture (FIG. 2). Assignments of cleavage site signals intermediates were conducted through comparison of the 2D spectra with reference assignments from previous work (Petersen et al 2013). These assignments show that the vastly predominating cleavage site signals can be attributed to β-(1-3) reducing end signals, formed by cleavage with an endo-1,3-1,4-β-D-glucanase (Lichenase, EC 3.2.1.73) activity in Attenuzyme® Flex and Attenuzyme® preparations. The presence of this activity rationalizes the rapid decay of β-glucan molecular weights due to its endoglucanase activity. According to the invention it may be advantageous to use the side activity of commercial Attenuzyme® Flex and Attenuzyme® preparations, as this activity permits the controlled degradation of barley β-glucans to desired viscosities.

Example 5a

Characterisation of β-glucan

The characterization and quantification of β-glucan from barley wort prepared essentially as described in Example 1 is described in this example. Wort was prepared from several different barley varieties including lys5f and various commercially available barley varieties. The total β-glucan content of the barley grains used is provided in Table 1 below.

TABLE 1

Percent of β-glucan in different barley varieties (replicate × 2)

| Barley ID FLOUR | Dry matter (%) | Conc. (mg/l) | β-Glucan content (% dry matter) |
|---|---|---|---|
| lys5f (batch 1) | 94 | 779.6 | 16.5 |
| lys5f (batch 1) | 94 | 737.6 | 15.7 |
| lys5f (batch 2) | 94 | 724.4 | 15.3 |
| lys5f (batch 2) | 94 | 724.1 | 15.2 |
| Colombus | 90 | 188.7 | 4.2 |
| Colombus | 90 | 177.2 | 3.6 |
| Chameleon | 91 | 208.6 | 4.6 |
| Chameleon | 91 | 217.6 | 4.7 |

The fluorimetric method (Brewing EBC standards,1994) is used to determine the content of β-glucan in wort as well as in barley grains. The apparatus used is a β-glucan Carlsberg System 5700 Analyzer, Tecator, Sweden, a flow injection analysis equipment using as a principle measurements of the changes in intensity of a calcofluor dye based on its binding capacity with the β-glucan. The calcofluor has the capacity to bind with β-glucan>10-30 kDa present in solution and increases its fluorescence in a direct proportion with the content of β-glucan bounded.

Figure 9:
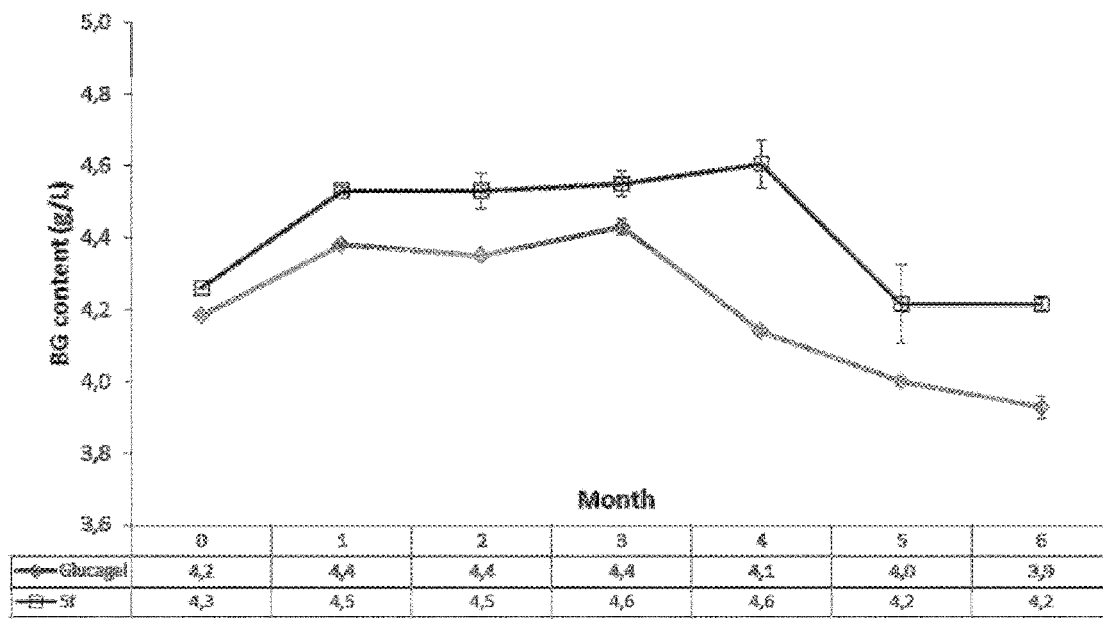
FIG. 9: stability of β-glucan content (g/L) in bottles stored at room temperature for 6 months. Glucagel™ and lys5f TAF suspensions measured by calcofluor Mean values±SD, n=2 per months.

The stability of β-glucan content was tested by storing wort (4 g/L of β-glucan) for 6 months at room temperature and regularly determining the β-glucan content using the calcoflour method described above. The β-glucan content of wort prepared from lys5f essentially as described in Example 1 and a solution of Glucagel™ were followed and the results shown in FIG. 9.

The viscosity of the wort was measured by viscometer Vibro SV-10 (A&D Company Limited, Tokyo) at 20° C. within 1 h from centrifugation of wort (as described in Example 1). The procedure followed was filling up the viscometer with 10 ml wort and recorded the value on the screen in mPas unit. The results are shown in Table 2.

TABLE 2

| Barley | flour:water | wort viscosity (mPas) |
|---|---|---|
| Chameleon | 1:15 | 2.7 |
| Colombus | 1:15 | 2.4 |
| lys5f (a) | 1:20 | 4.7 |
| lys5f (b) | 1:15 | 8.7 |
| lys5f (c) | 1:10 | 34.1 |

Viscosity (mPas) of wort from different barley varieties extracted by Termamyl ® SC + Attenuzyme ® Flex (TAF)

Figure 12:
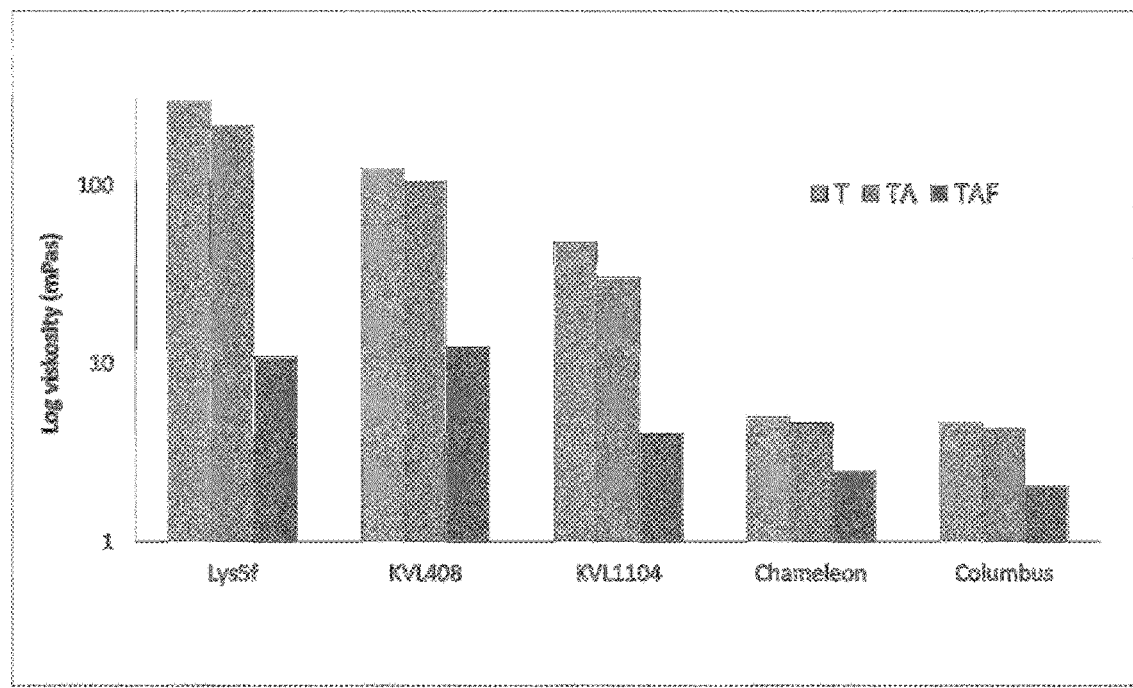
FIG. 12 shows the beta-glucan wort viscosity after the extraction of different barleys with T, TA, and TAF enzymes.

In addition, barley wort was prepared from different barley lines essentially as described in Example 1 after extraction using either a mixture of Termamyl® SC and Attenuzyme® Flex (TAF), or a mixture of Termamyl® SC and Attenuzyme® (TA) or Termamyl® (T). The viscosity of the worts was determined, and the results are shown in FIG. 12. Barley worts prepared using TAF have a very low viscosity.

Before analyzing molecular weight and DP3/DP4 ratio the β-glucans was precipitated from the wort using ethanol. The precipitation was done by mixing 1:1 wort prepared as described in Example 1 into 80% ethanol in a glass beaker at room temperature. The mixture was left for precipitation 30 min. The resulting β-glucan gums were collected by sieving and freeze dried 24 h. The β-glucan gums were taken out from the freeze drying, weighted and grinded into powder.

The molecular weight analysis was conducted by conventional size exclusion chromatography (SEC). Samples were applied on an asahipak GS 520HQ (7.5*300 mm) or asahipak GS 320HQ (7.5*300 mm) column (Shodex, US). The column was calibrated with five β-glucan standards; Barley BG 650000, oat BG 391000, oat BG 265000, barely BG 229000, oat BG 70600 and oat BG 35600 (from Megazyme, Ireland). Elutions were performed with 50 mM of $NH_4COOH$ buffer pH 5 and 0.01% $NaN_3$ at 60° C. with a constant flow rate of 0.5 ml/min. This separation was performed using a GPC system (viscotek 270max, Malvern) equipped with an online degasser, a pump and a differential refractometer controlled at 40° C. Powder sample was wet with 20 µl of 50% ethanol before dissolved in buffer. The solution with 1 mg/ml was heated up to 80° C. for 2 hours before centrifugation. All the samples were centrifuged and filtered (0.45 µm) before injection of 50 µl. Data for molecular weight determinations was analyzed by Omnisec software (version 4.7.0.406, Malvern) based on conversional calibration of homopolymers.

The results of molecular weight analysis of three β-glucans are shown in Table 3.

TABLE 3

Molecular weight averages (Mw) of selected β-glucans

| β-Glucan | Mw (kDa) |
|---|---|
| Glucagel ™ (DKSH) | 100 |
| lys5f TAF (extracted with Termamyl ® SC & Attenuzyme ® Flex) | 150 |
| lys5f TA (extracted with Termamyl ® SC & Attenuzyme ®) | 530 |

As described in Example 4, Attenuzyme Flex has endo-1,3-1,4-β-D-glucanase activity.

The DP3/DP4 ratio (cellotriose to cellotetraose) describes the β-glucan oligomer block structure. The DP3/DP4 analysis was based on the complete lichenase digestion of β-glucan precipitated from wort prepared as described above. The DP3/DP4 ratio was determined for β-glucans in worts prepared from various barley lines as well as for the commercial barley β-glucans Glucagel™. The assay mixture consisted of 2.5 mg β-glucan sample in 500 µl of 10 mM $NaH_2PO_4/Na_2HPO_4$ buffer and 110 µl of lichenase suspension (10 U) of lichenase (Megazyme, Ireland). The sample was wet with 10 µl of ethanol (50% V/V) before dissolved in the buffer. The solution was heated up to 96° C. for 2 h before adding lichenase. Sample was incubated overnight for 60° C. The enzyme was inactivated by a 30 min treatment in a boiling water bath.

Aminobenzamide (2-AB) is a common fluorescence label attached to reducing ends of oligosaccharides by a reductive amination procedure. 2-AB labelling: Fluorescence labelling with 2-aminobenzamide prior to UPLC analysis (waters) was performed on reference standards and samples as follows. Glucose, maltose, maltotriose, maltotetraose, and maltopentaose were dissolved in water to concentration of 1 mg/ml. 200 µl of this solution were lyophilized. 200 µl of each sample were lyophilized. To these solutions were added 200 µl of 2-AB and 200 µl of NaBH$_3$CN. Samples were whirlmixed and incubated overnight at 60° C., then cooled to room temperature, diluted with 3.6 ml H$_2$O and washed with CH$_2$Cl$_2$ (2×8 ml). Of each aqueous layer 1 ml was collected, centrifuged for 5 minutes and diluted 1 in 10 with a mixture of 10 mM ammonium format buffer (pH 4.5) and acetonitrile (22:78).

The results of DP3/DP4 ratio are shown in Table 4.

TABLE 4

DP3/DP4 ratio of β-glucan from selected barley varieties and Glucagel ™.

| BG of selected barley varieties | DP3/DP4 ratio |
|---|---|
| lys5f | 3.8 |
| Glucagel ™ (DKSH) | 3.1 |
| Chameleon | 2.7 |
| Colombus | 2.6 |

Chameleon and Columbus are commercially available barley varieties.

Figure 11:
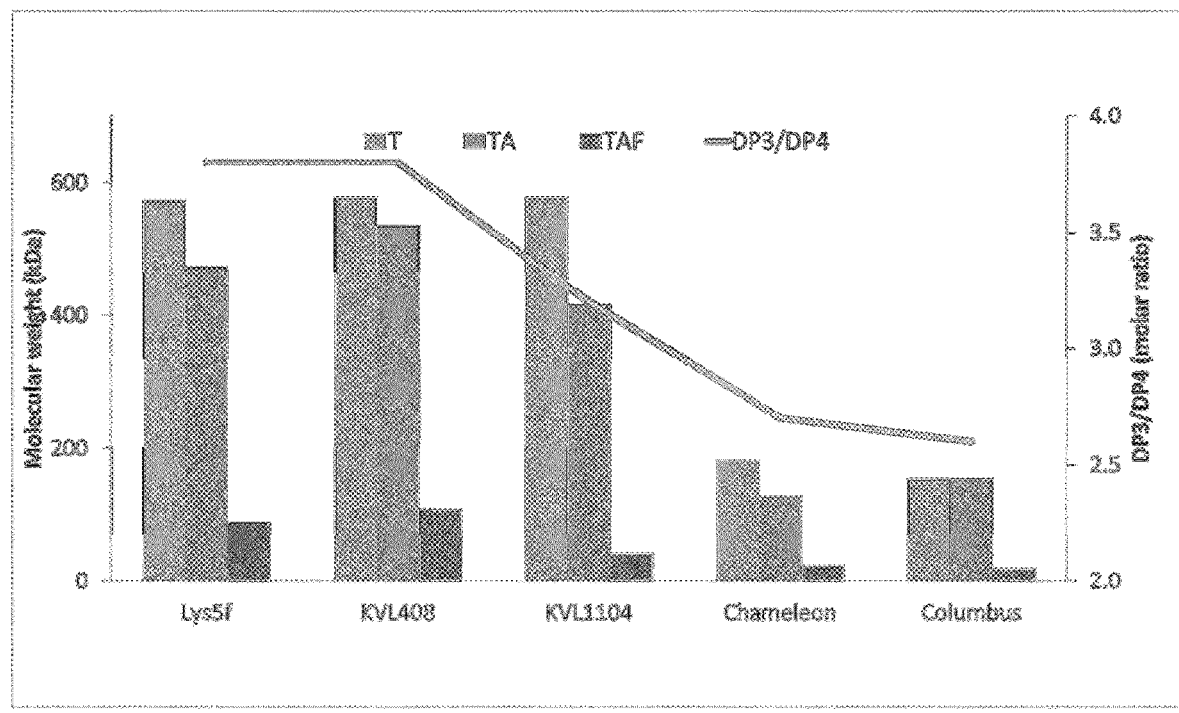
FIG. 11 shows the DP3/DP4 ratio in barley kernels of various barley lines, together with the Mw of β-glucans in wort said barley kernels using either a mixture of Termamyl® SC and Attenuzyme® Flex (TAF), or a mixture of Termamyl® SC and Attenuzyme® (TA) or Termamyl® (T).

Furthermore, FIG. 11 shows the DP3/DP4 ratio in barley kernels of various barley lines (indicated in the figure), together with the Mw of β-glucans in wort prepared from said barley kernels essentially as described in Example 1 after extraction using either a mixture of Termamyl® SC and Attenuzyme® Flex (TAF), or a mixture of Termamyl® SC and Attenuzyme® (TA) or Termamyl® (T).

Example 6

In Vitro Effects of β-Glucans from Wort

This study investigates how the molecular size of β-glucans affects the capacity of the polysaccharides to bind a bile salt in vitro. We used high-resolution $^1$H-$^{13}$C NMR (800 MHz) experiments as described by Mikkelsen et al. 2014 for probing the interactions between β-glucan and glycocholate at molecular detail. The β-glucans to be tested were:
  A. Low molecular weight lys5f TAF (LMw-150 kDa)—extracted with Termamyl® SC and Attenuzyme® Flex as described in Example 1
  B. Medium molecular weight lys5f TA (MMw-530 kDa)—extracted with Terrmamyl SC and Attenuzyme® as described in Example 1.

β-Glucan samples were dissolved (1% w/v) in 100 mM sodium acetate buffer of pH 5 in D$_2$O and hydrated at 99° C. for 30 min. Acetate buffer of pH 5 had been prepared in H$_2$O prior to lyophilization and redissolution in D$_2$O. The bile salt was mixed into the BG solution at concentrations; 0, 5, 15, 30, or 45 mM and the mixtures were incubated at 3° C. for 120 min. Following this incubation, the samples were transferred to 5 mm NMR sample tubes and analyzed at 37° C. by $^1$H-$^{13}$C heteronuclear single-quantum correlation (HSQC) experiments.

Absorption of bile salt to β-glucans was treated as a Langmuir adsorption isotherm and fitting of the chemical shift differences to the Langmuir adsorption model was used to qualitatively probe the effect of β-glucan molecular weight on interactions with glycocholate. The results are shown in FIG. 3.

The signal changes (Δδ) between two β-glucan resonances indicate direct interactions between β-glucans and the bile salt in solution. This is consistent with direct binding between glycocholate and the β-glucans produced by Termamyl® SC and Attenuzyme® treatment (lys5f TA in FIG. 3) and additional Attenuzyme® Flex treatment (lys5f TAF in FIG. 3). While bile salt adsorption to both β-glucans is detectable, the strength of bile salt binding did not vary significantly between the preparations. Hence, these in vitro results confirm that the 150 kDa lys5f TAF β-glucan retains the ability of the 530 kDa lys5f TA β-glucan to absorb bile salts through direct molecular interactions.

Example 7

In-Vivo Effects of β-Glucan of Wort

The objective of the animal study was to examine how the type and quality of β-glucan affects cholesterol metabolism in hypercholesterolemic rats. In this in vivo model we selected three different β-glucans with significantly different structure and molecular weight. The primary focus was the effect in lowering blood cholesterol. The study design started with a run-in period of 3 weeks on a high cholesterol diet (2%) (plus 0.5% cholic acid Na salt/bile salt), which has been found to induce hypercholesterolemia in male Wistar rats.

The trial feed was produced so all treatments contain the same amount of protein, fat, starch and fiber (5%). Furthermore, 2% cholesterol was added to the feed. Based on exact analyzes of protein, starch and dietary fibre in the β-glucan powder, the feed composition was adjusted so the daily feed total content of various nutritional components was identical.

The feed composition in the three experimental diets (A, B, C) was based on a high fat diet (fiber, see table 5) where the 5% fiber was provided from following 3 β-glucan products:
  A: Control β-glucan-Glucagel™ (DKSH)
  B: Low molecular weight lys5f TAF (LMw)—extracted with Termamyl® SC & Attenuzyme® Flex as described in Example 5a)
  C: Medium molecular weight lys5f TA (MMw)—extracted with Termamyl® SC & Attenuzyme® as described in Example 5a)

Low and medium molecular weight lys5f β-glucans weres prepared by precipitating β-glucans from wort. The wort was prepared as described in Example 1 using the barley lys5f and the precipitation was performed as described in Example 5a.

TABLE 5

High fat diet composition (% as is basis).

| Ingredients: | |
|---|---|
| White wheat flour | 42.0 |
| β-Glucan | — |
| Miprodan 30 casein | 19.0 |
| Sucrose | 12.0 |
| Soybean Oil | 5.0 |
| Lard | 10.0 |

TABLE 5-continued

High fat diet composition (% as is basis).

Ingredients:

| | |
|---|---|
| Cholesterol | 2.0 |
| Powdered Cellulose | 5.0 |
| AIN 93G Mineral Mix | 3.5 |
| AIN 93 Vitamin Mix | 1.0 |
| L-Cystine | 0.3 |
| Choline Bitartrate | 0.3 |
| % contribution | 100.1 |

The experiment used a total of 36 Wistar rats (12 per treatment) of 5 weeks old. The experiment was performed each 2 laps (blocks) with 24 or 12 rats, 2 weeks apart. On arrival the rats was marked with chips and distributed in boxes (4/6 per box). After arrival rats was fed ad lib with AIN93G standard feed (pellets), then fed ad libitum with the high fat diet test feed for 3 weeks. Feed intake per box (4-5 animals) was recorded weekly.

After week 3 animals were weighed and taken tail blood under general anesthesia to blood lipid analysis. Animals were randomized to the 3 treatments referred weight (similar mean weight per treat) and housed 4 animals per box (one box per treatment per block) and fed ad libitum. The feed and weight recorded weekly.

After week 5 rats were housed individually in the metabolic cages. After 3 days of habituation the digestibility trials with daily addition of 20 g feed/day was carried out. A total amount of feed (80 g) was allocated and fertilizers produced were collected in one bag.

After week 7 the rat is weighed and killed under anesthesia. Blood is collected for analysis of:
Plasma triglyceride, Plasma total cholesterol, Plasma HDL, Plasma LDL, Content from stomach analyzed in terms of solids %. Content from appendicitis analyzed in terms of content of volatile fatty acids.
Manure from balance study was freeze-dried and analyzed in terms of dry matter and ash.

Results on changes in lipid profile after treatment shown in FIG. 4-7. All lipids were analyzed on Pentra 400. Because low-density lipoprotein (LDL) cholesterol is a major risk factor for heart disease, it is preferred that the LDL levels are reduced, Similarly, it is preferred that the total cholesterol levels are reduced However, High-density lipoprotein (HDL) cholesterol is known as "good" cholesterol because it helps prevent arteries from becoming clogged, and therefore it is preferred that the level of HDL does not decrease.

Figure 8:
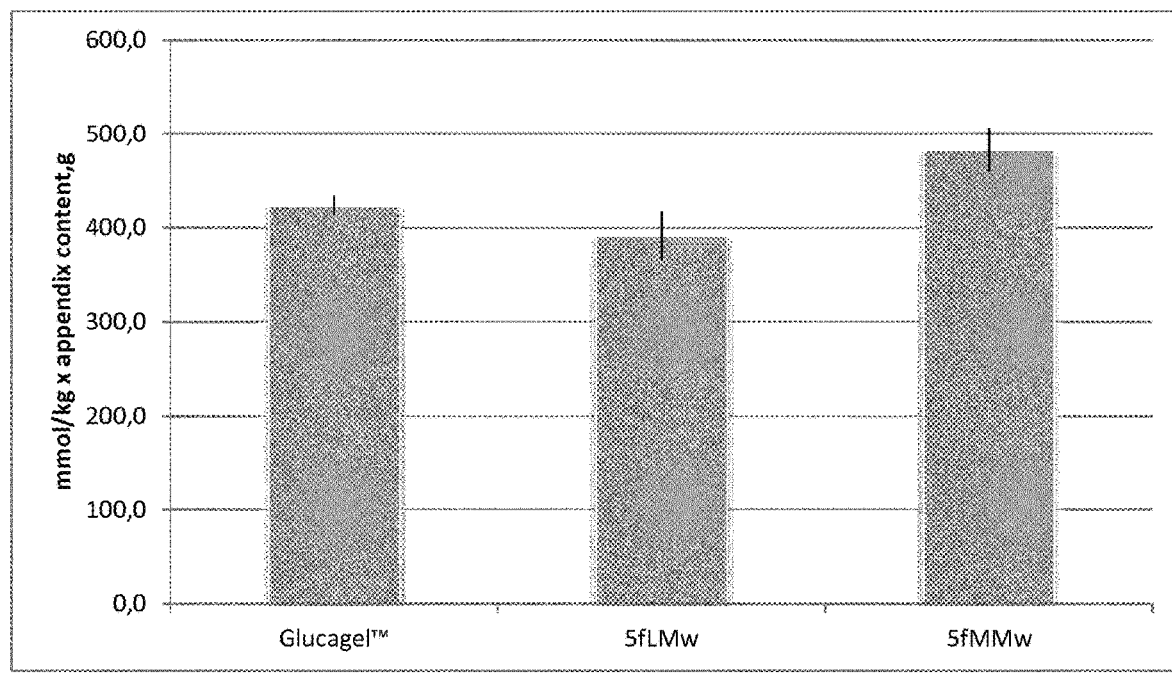
FIG. 8: differences in total SCFA pool (mmol/kg) by appendix content (g) after 4 weeks β-glucan treatment in rats. Mean values±SEM n=12 per treatment

Numerical changes in total SCFA pool was observed after treatments see FIG. 8. Calculation of total amount of SCFA=butyric acid, propionic acid, and acetic acids (mmol in wet sample, kg)×weight (gr) of appendix content.

The statistical analysis showed significant difference in total SCFA pool between the experimental β-glucan treatments (LMw lys5f, MMw lys5f), and the commercial available barley β-glucan Glucagel™. The increase in total SCFA after β-glucan treatments is considered beneficial as SOFA have been linked to cholesterol lowering mechanism and function as energy source for colonic cells and is important for gut health.

Example 8

Barley wort was prepared by mashing barley flour in the following mixtures:
Wort recipe trial 1
27 g flour of barley variety Lys5f
400 ml water (tap)
530 ul 25% phosphoric acid
120 ul 35% calciumchloride
800 ul Termamyl® Sc
4 ul β-glucanase (Attenuzyme® flex or Ultraflo® max)
Wort recipe trial 2
27 g flour of barley variety Lys5f
400 ml water (tap)
530 ul 25% phosphoric acid
120 ul 35% calciumchloride
800 ul Termamyl Sc
0.4 ul beta-glucanase (Attenuzyme flex or Ultraflo max)
Wort recipe trial 3
27 g flour of barley variety Lys5f
400 ml water (tap)
530 ul 25% phosphoric acid
120 ul 35% calciumchloride
800 ul Termamyl Sc
0.04 ul beta-glucanase (Attenuzyme flex or Ultraflo max)

Termamyl® SC, Attenuzyme® Flex or with Ultraflo® max are available from Novozymes, Denmark. In order to prepare the low amounts of enzymes used a dilution of 100 ul enzyme+9,9 ml water was made, however the indicated amounts correspond to the volume of original enzyme preparation.

The mashing was performed by mashing-in at 65° C. in a 500 ml metal beaker. After 45 min at 65° C., the temperature was gradually increased to 90° C. during a 25 min period, and finally kept at 90° C. for 30 min. The mash was centrifuged at 5000 rpm for 15 min at room temperature (20-24° C.) to remove insoluble spent grain material.

The viscosity and the content of beta-glucan were determined essentially as described herein above in Example 5. The results are shown in Table 6.

TABLE 6

| β-glucanase | Volumen of β-glucanase, μl | Viscosity, mPas | β-glucan g/L* |
|---|---|---|---|
| Attenuzyme flex | 4 | 50.6 | 10,940 |
| | 0.4 | 52.3 | 11,528 |
| | 0.04 | 46.3 | 9,826 |
| Ultraflo max | 4 | 4.36 | 4,080 |
| | 0.4 | 23.8 | 9,684 |
| | 0.04 | 52.1 | 10,856 |

According to manufacturer Attenuzyme® Flex comprises glucoamylase, α-amylase and pullulanase. However, as described in Example 4 herein above Attenuzyme® Flex also comprises a β-glucanase side activity. When Attenuzyme® Flex is applied in very low amounts, the resulting wort has a viscosity in the higher end of the acceptable range. However, as shown in Example 5a when using higher amounts of Attenuzyme® Flex, wort with lower viscosity is obtained.

According to manufacturer, Ultraflo® Max comprises β-glucanase (700 EGU/g) and xylanase (250 FXU/g). As used herein EGU is an abbreviation for endoglucanase units. When applying approximately 0.28 EGU Ultraflo® Max per 27 g barley (corresponding to 0.01 EGU/g barley), wort with an acceptable β-glucan concentration and viscosity is obtained. When applying approximately 2.8 EGU Ultraflo® Max per 27 g barley (corresponding to 0.1 EGU/g barley), wort with a lower, but still acceptable β-glucan concentration and viscosity is obtained. When applying approximately 0.028 EGU Ultraflo® Max per 27 g barley (corresponding to 0.001 EGU/g barley), wort with an acceptable β-glucan concentration is obtained, which has a viscosity in higher end of the acceptable range.

The invention claimed is:

1. A method for preparing a beverage comprising at least 2 g/L β-glucans, wherein said β-glucans have an average molecular weight in the range of 110 to 200 kDa, said method comprising the steps of
   a) providing kernels of a barley plant, wherein said kernels have the following characteristics:
      i. comprising at least 10% β-glucans; and
      ii. having a ratio of DP3/DP4 in said β-glucans of at least 3.4;
   b) mashing said kernels with water in the presence of an enzyme composition, wherein said enzyme composition comprises α-amylase and endo-1,3(4)-β-glucanase activity, thereby obtaining an aqueous extract; and
   c) separating said aqueous extract from the barley kernels, thereby obtaining a beverage or a beverage base.

2. The method according to claim 1, wherein the enzyme composition further comprises a glucoamylase activity.

3. The method according to claim 1, wherein the enzyme composition further comprises a pullulanase activity.

4. The method according to claim 1, wherein the beverage comprises at least 3 g/L β-glucans.

5. The method according to claim 1, wherein said kernels comprise at least 11% β-glucans.

6. The method according to claim 1, wherein the ratio of DP3/DP4 in said β-glucans is at least 3.6.

7. The method according to claim 1, wherein the barley plant carries a mutation in the HvNst1 gene.

8. The method according to claim 1, wherein step b) comprises mixing milled barley kernels with water at a ratio of water to milled barley of 1 to in the range of 10 to 20.

9. The method according to claim 1, wherein the beverage has a viscosity of at the most 50 mPas.

10. The method according to claim 1, wherein a beverage base is obtained in step c), and further comprising step d) processing the beverage base into a beverage.

11. The method according to claim 10, wherein the step d) comprises adding one or more additional compounds and/or one or more additional liquids to the beverage base obtained in step c) in order to produce a beverage.

12. The method according to claim 11, wherein at least one additional compound is added, which is selected from the group consisting of a flavor compound, a preservative, and a functional ingredient; or wherein at least one additional liquid is added, which is selected from the group consisting of fruit juice, water, and beer.

13. The method according to claim 10, wherein step d) comprises fermenting the beverage base with one or more microorganisms.

14. A beverage comprising at least 2 g/L β-glucans, wherein said β-glucans have an average molecular weight in the range of 110 to 200 kDa and wherein said beverage is produced by the method according to claim 1.

15. The beverage according to claim 14, wherein the beverage has a viscosity of at the most 50 mPas.

16. A method for reducing the risk of acquiring a clinical condition in an individual in need thereof, wherein the clinical condition is selected from the group consisting of coronary heart disease, diabetes, and infections, said method comprising administering the beverage according to claim 14 to said individual in an effective amount.

17. A method for reducing blood levels of at least one lipid selected from the group consisting of triglycerides, cholesterol, and LDL in an individual in need thereof, wherein said method comprises intake of the beverage according to claim 14 by said individual.

18. The method according to claim 16, wherein said individual is administered beverage comprising at least 3 g β-glucan daily.

19. A method for reducing the risk of obesity or reducing obesity in an individual in need thereof, said method comprising intake by said individual of the beverage according to claim 14.

20. The method according to claim 17, wherein the individual is a human being.

* * * * *

SEQUENCE LISTING

<160> NUMBER OF SEQ ID NOS: 5

<210> SEQ ID NO 1
<211> LENGTH: 425
<212> TYPE: PRT
<213> ORGANISM: Hordeum vulgare

<400> SEQUENCE: 1

```
Met Ala Ala Ala Met Ala Ala Thr Thr Met Val Thr Lys Asn Asn Gly
1               5                   10                  15

Gly Ser Leu Ala Met Asp Lys Lys Asn Trp Phe Phe Arg Pro Ala Pro
            20                  25                  30

Glu Val Ala Phe Ser Trp Ser Ser Gln Pro Glu Ser Arg Ser Leu Glu
        35                  40                  45

Phe Pro Arg Arg Ala Leu Phe Ala Ser Val Gly Leu Ser Leu Ser His
    50                  55                  60

Asp Gly Lys Ala Arg Pro Ala Asp Val Ala His Gln Leu Ala Ala
65                  70                  75                  80

Ala Gly Asp Ala Gly Val Gln Gln Ala Gln Lys Ala Lys Lys Ala Lys
                85                  90                  95

Lys Gln Gln Leu Gly Leu Arg Lys Val Arg Val Lys Ile Gly Asn Pro
            100                 105                 110

His Leu Arg Arg Leu Val Ser Gly Ala Ile Ala Gly Ala Val Ser Arg
        115                 120                 125

Thr Phe Val Ala Pro Leu Glu Thr Ile Arg Thr His Leu Met Val Gly
    130                 135                 140

Ser Ser Gly Ala Asp Ser Met Gly Gly Val Phe Arg Trp Ile Met Arg
145                 150                 155                 160

Thr Glu Gly Trp Pro Gly Leu Phe Arg Gly Asn Ala Val Asn Val Leu
                165                 170                 175

Arg Val Ala Pro Ser Lys Ala Ile Glu His Phe Thr Tyr Asp Thr Ala
            180                 185                 190

Lys Lys Tyr Leu Thr Pro Glu Ala Gly Glu Pro Ala Lys Val Pro Ile
        195                 200                 205

Pro Thr Pro Leu Val Ala Gly Ala Leu Ala Gly Val Ala Ser Thr Leu
    210                 215                 220

Cys Thr Tyr Pro Met Glu Leu Val Lys Thr Arg Leu Thr Ile Glu Lys
225                 230                 235                 240

Asp Val Tyr Asp Asn Leu Leu His Ala Phe Val Lys Ile Val Arg Asp
                245                 250                 255

Glu Gly Pro Gly Glu Leu Tyr Arg Gly Leu Ala Pro Ser Leu Ile Gly
            260                 265                 270

Val Val Pro Tyr Ala Ala Ala Asn Phe Tyr Ala Tyr Glu Thr Leu Arg
        275                 280                 285

Gly Ala Tyr Arg Arg Ala Ser Gly Lys Glu Glu Val Gly Asn Val Pro
    290                 295                 300

Thr Leu Leu Ile Gly Ser Ala Ala Gly Ala Ile Ala Ser Thr Ala Thr
305                 310                 315                 320

Phe Pro Leu Glu Val Ala Arg Lys Gln Met Gln Val Gly Ala Val Gly
                325                 330                 335

Gly Arg Gln Val Tyr Lys Asn Val Leu His Ala Met Tyr Cys Ile Leu
            340                 345                 350

Asn Lys Glu Gly Ala Ala Gly Leu Tyr Arg Gly Leu Gly Pro Ser Cys
        355                 360                 365
```

```
Ile Lys Leu Met Pro Ala Ala Gly Ile Ser Phe Met Cys Tyr Glu Ala
        370                 375                 380

Cys Lys Lys Ile Leu Val Asp Asp Lys Gln Asp Gly Glu Pro Gln Asp
385                 390                 395                 400

Gln Glu Glu Thr Glu Thr Gly His Thr Gln Gly Gln Ala Ala Pro Lys
                405                 410                 415

Ser Pro Asn Ala Asn Gly Asp Arg Pro
        420                 425

<210> SEQ ID NO 2
<211> LENGTH: 1278
<212> TYPE: DNA
<213> ORGANISM: Hordeum vulgare

<400> SEQUENCE: 2
atggcggcgg caatggctgc aacgacaatg gtgaccaaga caacggcgg ctcgctcgcc      60 atggacaaga gaactggtt ctttcggccg gcccctgagg tcgccttctc ttggagctcg     120
cagcccgagt ccaggagctt ggagttccca cgcaggctc tgttcgccag cgtcggactc     180
agcctgtccc acgacgggaa ggctcggccc gccgacgacg tcgcacacca actcgcagcc     240
gcgggcgatg cgggcgtcca gcaggcccag aaggcgaaaa aggccaagaa gcagcagctg     300
ggtctgagga aggtgagggt caagatcggc aacccgcacc tgcgtcggct ggtcagcggc     360
gccatcgccg cgccgtttc gaggactttc gtggcgccgc tggagacgat caggacgcac     420
ctgatggtgg aagctccgg cgccgactcc atgggcgggg ttttccggtg gatcatgagg     480
acggaggggt ggcccggcct cttccgcggc aacgccgtca acgtcctccg cgtcgcgccg     540
agcaaggcca tcgagcactt cacttacgac acggccaaga agtacctgac cccggaggcc     600
ggcgagccag ccaaggtccc catccccacg ccgcttgtcg ccggagcgct cgccggagtg     660
gcctcaaccc tgtgcaccta tcccatggag ctcgtcaaga cccgtctcac catcgagaag     720
gatgtgtacg acaacctcct ccacgcgttc gtcaagatcg tgcgcgacga ggggcccgga     780
gagctgtacc gcgggctggc cgcagcctg atcggcgtgg tgccgtacgc ggcggccaac     840
ttctacgcct acgagacact gcggggcgcg taccgccgcg cgtcggggaa ggaggaggtg     900
ggcaacgtgc cgacgctgct gatcgggtcc gcggcgggcg ccatcgccag cacggccacc     960
ttcccgctgg aggtggcgcg gaagcagatg caggtgggcg ccgtgggcgg gaggcaggtg    1020
tacaagaacg tcctgcacgc catgtactgc atcctcaaca aggagggcgc cgccgggctc    1080
taccgcgggc tcggcccag ctgcatcaag ctcatgcccg ccgccggcat ctccttcatg    1140
tgctacgagg cctgcaagaa gatactcgtc gacgacaaac aagacggcga gccccaggac    1200
caggaggaga cggagaccgg acacacacaa ggacaggcgg cgcccaagag ccccaacgcc    1260
aacggtgatc gaccatga                                                1278

<210> SEQ ID NO 3
<211> LENGTH: 512
<212> TYPE: PRT
<213> ORGANISM: Bacillus stearothermophilus

<400> SEQUENCE: 3

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
```

-continued

```
                35                  40                  45
Gly Thr Ser Arg Ser Asp Val Gly Tyr Gly Val Tyr Asp Leu Tyr Asp
 50                  55                  60
Leu Gly Glu Phe Asn Gln Lys Gly Ala Val Arg Thr Lys Tyr Gly Thr
 65                  70                  75                  80
Lys Ala Gln Tyr Leu Gln Ala Ile Gln Ala His Ala Ala Gly Met
                 85                  90                  95
Gln Val Tyr Ala Asp Val Val Phe Asp His Lys Gly Gly Ala Asp Gly
                100                 105                 110
Thr Glu Trp Val Asp Ala Val Glu Val Asn Pro Ser Asp Arg Asn Gln
                115                 120                 125
Glu Ile Ser Gly Thr Tyr Gln Ile Gln Ala Trp Thr Lys Phe Asp Phe
                130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                165                 170                 175
Lys Phe Arg Gly Lys Ala Trp Asp Trp Glu Val Asp Thr Glu Phe Gly
                180                 185                 190
Asn Tyr Asp Tyr Leu Met Tyr Ala Asp Leu Asp Met Asp His Pro Glu
                195                 200                 205
Val Val Thr Glu Leu Lys Ser Trp Gly Lys Trp Tyr Val Asn Thr Thr
210                 215                 220
Asn Ile Asp Gly Phe Arg Leu Asp Ala Val Lys His Ile Lys Phe Ser
225                 230                 235                 240
Phe Phe Pro Asp Trp Leu Ser Asp Val Arg Ser Gln Thr Gly Lys Pro
                245                 250                 255
Leu Phe Thr Val Gly Glu Tyr Trp Ser Tyr Asp Ile Asn Lys Leu His
                260                 265                 270
Asn Tyr Ile Met Lys Thr Asn Gly Thr Met Ser Leu Phe Asp Ala Pro
                275                 280                 285
Leu His Asn Lys Phe Tyr Thr Ala Ser Lys Ser Gly Gly Thr Phe Asp
290                 295                 300
Met Arg Thr Leu Met Thr Asn Thr Leu Met Lys Asp Gln Pro Thr Leu
305                 310                 315                 320
Ala Val Thr Phe Val Asp Asn His Asp Thr Glu Pro Gly Gln Ala Leu
                325                 330                 335
Gln Ser Trp Val Asp Pro Trp Phe Lys Pro Leu Ala Tyr Ala Phe Ile
                340                 345                 350
Leu Thr Arg Gln Glu Gly Tyr Pro Cys Val Phe Tyr Gly Asp Tyr Tyr
                355                 360                 365
Gly Ile Pro Gln Tyr Asn Ile Pro Ser Leu Lys Ser Lys Ile Asp Pro
                370                 375                 380
Leu Leu Ile Ala Arg Arg Asp Tyr Ala Tyr Gly Thr Gln His Asp Tyr
385                 390                 395                 400
Leu Asp His Ser Asp Ile Ile Gly Trp Thr Arg Glu Gly Val Thr Glu
                405                 410                 415
Lys Pro Gly Ser Gly Leu Ala Ala Leu Ile Thr Asp Gly Pro Gly Gly
                420                 425                 430
Ser Lys Trp Met Tyr Val Gly Lys Gln His Ala Gly Lys Val Phe Tyr
                435                 440                 445
Asp Leu Thr Gly Asn Arg Ser Asp Thr Val Thr Ile Asn Ser Asp Gly
450                 455                 460
```

```
Trp Gly Glu Phe Lys Val Asn Gly Gly Ser Val Ser Val Trp Val Pro
465                 470                 475                 480

Arg Lys Thr Thr Val Ser Thr Ile Ala Trp Ser Ile Thr Thr Arg Pro
                485                 490                 495

Trp Thr Asp Glu Phe Val Arg Thr Glu Pro Arg Leu Val Ala Trp
            500                 505                 510

<210> SEQ ID NO 4
<211> LENGTH: 862
<212> TYPE: PRT
<213> ORGANISM: Bacillus acidopullulyticus

<400> SEQUENCE: 4

Met Ser Leu Ile Arg Ser Arg Tyr Asn His Phe Val Ile Leu Phe Thr
1               5                   10                  15

Val Ala Ile Met Phe Leu Thr Val Cys Phe Pro Ala Tyr Lys Ala Leu
            20                  25                  30

Ala Asp Ser Thr Ser Thr Glu Val Ile Val His Tyr His Arg Phe Asp
        35                  40                  45

Ser Asn Tyr Ala Asn Trp Asp Leu Trp Met Trp Pro Tyr Gln Pro Val
50                  55                  60

Asn Gly Asn Gly Ala Ala Tyr Glu Phe Ser Gly Lys Asp Asp Phe Gly
65                  70                  75                  80

Val Lys Ala Asp Val Gln Val Pro Gly Asp Thr Gln Val Gly Leu
                85                  90                  95

Ile Val Arg Thr Asn Asp Trp Ser Gln Lys Asn Thr Ser Asp Asp Leu
            100                 105                 110

His Ile Asp Leu Thr Lys Gly His Glu Ile Trp Ile Val Gln Gly Asp
        115                 120                 125

Pro Asn Ile Tyr Tyr Asn Leu Ser Asp Ala Gln Ala Ala Ala Thr Pro
130                 135                 140

Lys Val Ser Asn Ala Tyr Leu Asp Asn Glu Lys Thr Val Leu Ala Lys
145                 150                 155                 160

Leu Thr Asn Pro Met Thr Leu Ser Asp Gly Ser Ser Gly Phe Thr Val
                165                 170                 175

Thr Asp Lys Thr Thr Gly Glu Gln Ile Pro Val Thr Ala Ala Thr Asn
            180                 185                 190

Ala Asn Ser Ala Ser Ser Glu Gln Thr Asp Leu Val Gln Leu Thr
        195                 200                 205

Leu Ala Ser Ala Pro Asp Val Ser His Thr Ile Gln Val Gly Ala Ala
    210                 215                 220

Gly Tyr Glu Ala Val Asn Leu Ile Pro Arg Asn Val Leu Asn Leu Pro
225                 230                 235                 240

Arg Tyr Tyr Tyr Ser Gly Asn Asp Leu Gly Asn Val Tyr Ser Asn Lys
                245                 250                 255

Ala Thr Ala Phe Arg Val Trp Ala Pro Thr Ala Ser Asp Val Gln Leu
            260                 265                 270

Leu Leu Tyr Asn Ser Glu Thr Gly Pro Val Thr Lys Gln Leu Glu Met
        275                 280                 285

Gln Lys Ser Asp Asn Gly Thr Trp Lys Leu Lys Val Pro Gly Asn Leu
    290                 295                 300

Lys Asn Trp Tyr Tyr Leu Tyr Gln Val Thr Val Asn Gly Lys Thr Gln
305                 310                 315                 320

Thr Ala Val Asp Pro Tyr Val Arg Ala Ile Ser Val Asn Ala Thr Arg
```

```
                      325                 330                 335
Gly Met Ile Val Asp Leu Glu Asp Thr Asn Pro Pro Gly Trp Lys Glu
                340                 345                 350
Asp His Gln Gln Thr Pro Ala Asn Pro Val Asp Glu Val Ile Tyr Glu
                355                 360                 365
Val His Val Arg Asp Phe Ser Ile Asp Ala Asn Ser Gly Met Lys Asn
                370                 375                 380
Lys Gly Lys Tyr Leu Ala Phe Thr Glu His Gly Thr Lys Gly Pro Asp
385                 390                 395                 400
Asn Val Lys Thr Gly Ile Asp Ser Leu Lys Glu Leu Gly Ile Asn Ala
                405                 410                 415
Val Gln Leu Gln Pro Ile Glu Glu Phe Asn Ser Ile Asp Glu Thr Gln
                420                 425                 430
Pro Asn Met Tyr Asn Trp Gly Tyr Asp Pro Arg Asn Tyr Asn Val Pro
                435                 440                 445
Glu Gly Ala Tyr Ala Thr Thr Pro Glu Gly Thr Ala Arg Ile Thr Gln
                450                 455                 460
Leu Lys Gln Leu Ile Gln Ser Ile His Lys Asp Arg Ile Ala Ile Asn
465                 470                 475                 480
Met Asp Val Val Tyr Asn His Thr Phe Asn Val Gly Val Ser Asp Phe
                485                 490                 495
Asp Lys Ile Val Pro Gln Tyr Tyr Arg Thr Asp Ser Ala Gly Asn
                500                 505                 510
Tyr Thr Asn Gly Ser Gly Val Gly Asn Glu Ile Ala Thr Glu Arg Pro
                515                 520                 525
Met Val Gln Lys Phe Val Leu Asp Ser Val Lys Tyr Trp Val Lys Glu
                530                 535                 540
Tyr His Ile Asp Gly Phe Arg Phe Asp Leu Met Ala Leu Leu Gly Lys
545                 550                 555                 560
Asp Thr Met Ala Lys Ile Ser Lys Glu Leu His Ala Ile Asn Pro Gly
                565                 570                 575
Ile Val Leu Tyr Gly Glu Pro Trp Thr Gly Gly Thr Ser Gly Leu Ser
                580                 585                 590
Ser Asp Gln Leu Val Thr Lys Gly Gln Gln Lys Gly Leu Gly Ile Gly
                595                 600                 605
Val Phe Asn Asp Asn Ile Arg Asn Gly Leu Asp Gly Asn Val Phe Asp
                610                 615                 620
Lys Ser Ala Gln Gly Phe Ala Thr Gly Asp Pro Asn Gln Val Asn Val
625                 630                 635                 640
Ile Lys Asn Gly Val Met Gly Ser Ile Ser Asp Phe Thr Ser Ala Pro
                645                 650                 655
Ser Glu Thr Ile Asn Tyr Val Thr Ser His Asp Asn Met Thr Leu Trp
                660                 665                 670
Asp Lys Ile Ser Ala Ser Asn Pro Asn Asp Thr Gln Ala Asp Arg Ile
                675                 680                 685
Lys Met Asp Glu Leu Ala Gln Ala Val Val Phe Thr Ser Gln Gly Val
                690                 695                 700
Pro Phe Met Gln Gly Gly Glu Glu Met Leu Arg Thr Lys Gly Gly Asn
705                 710                 715                 720
Asp Asn Ser Tyr Asn Ala Gly Asp Ser Val Asn Gln Phe Asp Trp Ser
                725                 730                 735
Arg Lys Ala Gln Phe Glu Asn Val Phe Asp Tyr Tyr Ser Trp Leu Ile
                740                 745                 750
```

```
His Leu Arg Asp Asn His Pro Ala Phe Arg Met Thr Thr Ala Asp Gln
        755                 760                 765

Ile Lys Gln Asn Leu Thr Phe Leu Asp Ser Pro Thr Asn Thr Val Ala
        770                 775                 780

Phe Glu Leu Lys Asn His Ala Asn His Asp Lys Trp Lys Asn Ile Ile
785                 790                 795                 800

Val Met Tyr Asn Pro Asn Lys Thr Ala Gln Thr Leu Thr Leu Pro Ser
                    805                 810                 815

Gly Asn Trp Thr Ile Val Gly Leu Gly Asn Gln Val Gly Glu Lys Ser
                820                 825                 830

Leu Gly His Val Asn Gly Thr Val Glu Val Pro Ala Leu Ser Thr Ile
        835                 840                 845

Ile Leu His Gln Gly Thr Ser Glu Asp Val Ile Asp Gln Asn
        850                 855                 860

<210> SEQ ID NO 5
<211> LENGTH: 242
<212> TYPE: PRT
<213> ORGANISM: Bacillus subtitlis

<400> SEQUENCE: 5

Met Pro Tyr Leu Lys Arg Val Leu Leu Leu Val Thr Gly Leu Phe
1               5                   10                  15

Met Ser Leu Phe Ala Val Thr Ala Thr Ala Ser Ala Gln Thr Gly Gly
                20                  25                  30

Ser Phe Phe Asp Pro Phe Asn Gly Tyr Asn Ser Gly Phe Trp Gln Lys
            35                  40                  45

Ala Asp Gly Tyr Ser Asn Gly Asn Met Phe Asn Cys Thr Trp Arg Ala
        50                  55                  60

Asn Asn Val Ser Met Thr Ser Leu Gly Glu Met Arg Leu Ala Leu Thr
65                  70                  75                  80

Ser Pro Ala Tyr Asn Lys Phe Asp Cys Gly Glu Asn Arg Ser Val Gln
                85                  90                  95

Thr Tyr Gly Tyr Gly Leu Tyr Glu Val Arg Met Lys Pro Ala Lys Asn
            100                 105                 110

Thr Gly Ile Val Ser Ser Phe Phe Thr Tyr Thr Gly Pro Thr Asp Gly
        115                 120                 125

Thr Pro Trp Asp Glu Ile Asp Ile Glu Phe Leu Gly Lys Asp Thr Thr
130                 135                 140

Lys Val Gln Phe Asn Tyr Tyr Thr Asn Gly Ala Gly Asn His Glu Lys
145                 150                 155                 160

Ile Val Asp Leu Gly Phe Asp Ala Ala Asn Ala Tyr His Thr Tyr Ala
                165                 170                 175

Phe Asp Trp Gln Pro Asn Ser Ile Lys Trp Tyr Val Asp Gly Gln Leu
            180                 185                 190

Lys His Thr Ala Thr Asn Gln Ile Pro Thr Thr Pro Gly Lys Ile Met
        195                 200                 205

Met Asn Leu Trp Asn Gly Thr Gly Val Asp Glu Trp Leu Gly Ser Tyr
210                 215                 220

Asn Gly Val Asn Pro Leu Tyr Ala His Tyr Asp Trp Val Arg Tyr Thr
225                 230                 235                 240

Lys Lys
```